(12) United States Patent
Qimron et al.

(10) Patent No.: US 8,865,158 B2
(45) Date of Patent: Oct. 21, 2014

(54) BACTERIOPHAGES FOR REDUCING TOXICITY OF BACTERIA

(75) Inventors: Ehud Qimron, Tel Aviv (IL); Rotem Edgar, Kfar-Saba (IL); Nir Friedman, Nes Ziona (IL)

(73) Assignee: Ramot at Tel-Aviv University Ltd., Tel Aviv (IL)

( * ) Notice: Subject to any disclaimer, the term of this patent is extended or adjusted under 35 U.S.C. 154(b) by 0 days.

(21) Appl. No.: 13/477,213

(22) Filed: May 22, 2012

(65) Prior Publication Data
US 2013/0315869 A1     Nov. 28, 2013

(51) Int. Cl.
*C12N 7/00* (2006.01)

(52) U.S. Cl.
USPC ............... 424/93.6; 435/235.1; 435/252.3; 435/264; 435/320.1

(58) Field of Classification Search
USPC ......... 424/93.6; 435/235.1, 252.3, 264, 320.1
See application file for complete search history.

(56) References Cited

U.S. PATENT DOCUMENTS

| | | |
|---|---|---|
| 3,791,932 A | 2/1974 | Schuurs et al. |
| 3,839,153 A | 10/1974 | Schuurs et al. |
| 3,850,578 A | 11/1974 | McConnell |
| 3,850,752 A | 11/1974 | Schuurs et al. |
| 3,853,987 A | 12/1974 | Dreyer |
| 3,879,262 A | 4/1975 | Schuurs et al. |
| 3,901,654 A | 8/1975 | Gross |
| 3,935,074 A | 1/1976 | Rubenstein et al. |
| 3,984,553 A | 10/1976 | Seng et al. |
| 3,996,345 A | 12/1976 | Ullman et al. |
| 4,034,074 A | 7/1977 | Miles |
| 4,098,876 A | 7/1978 | Piasio et al. |
| 4,666,828 A | 5/1987 | Gusella |
| 4,683,202 A | 7/1987 | Mullis |
| 4,801,531 A | 1/1989 | Frossard |
| 4,879,219 A | 11/1989 | Wands et al. |
| 5,011,771 A | 4/1991 | Bellet et al. |
| 5,192,659 A | 3/1993 | Simons |
| 5,272,057 A | 12/1993 | Smulson et al. |
| 5,281,521 A | 1/1994 | Trojanowski et al. |
| 5,645,991 A * | 7/1997 | Berg et al. ................ 435/6.18 |
| 2007/0059768 A1* | 3/2007 | Gill et al. .................. 435/7.1 |
| 2010/0322903 A1* | 12/2010 | Collins et al. ............. 424/93.2 |

FOREIGN PATENT DOCUMENTS

| | | | | |
|---|---|---|---|---|
| WO | WO 01/12803 | * | 2/2001 | ............ C12N 15/11 |
| WO | WO 2006/075996 | * | 7/2006 | ............ C12N 15/10 |
| WO | WO 2011/084647 | * | 7/2011 | ............ C12N 15/09 |

OTHER PUBLICATIONS

Westwater et al, Antimicrob. Agents & Chemo. 47(4):1301-1307, 2003.*
Cheng et al, Appl. Microbiol. Biotechnol. 74:1284-1291, 2007.*
Agilent Technologies, Uni-ZAP Vector Kit Instruction Manual, 2010.*
Cheng et al. "Specific gene silencing by artificial trans-encoded small noncoding RNAs in bacteria", Nucleic Acids Research, p. 1-15, May 27, 2009.
Edgar et al. "Reversing Bacterial Resistance to Antibiotics by Phage-Mediated Delivery of Dominant Sensitive Genes", Applied Environmental Microbiology, 78(3): 744-751, Feb. 2012.
Hagens et al. Genetically modified filamentous phage as bactericidal agents: a pilot study. Lett Appl Microbiol. 2003; 37(4):318-23.
Lederberg. "Streptomycin Resistance: A Genetically Recessive Mutation", J. Bacteriol. May 1951 61:549-550.
Lu et al. "Engineered bacteriophage targeting gene networks as adjuvants for antibiotic therapy" Proc Natl Acad Sci U S A Mar. 24, 2009;106(12):4629-34.
Nakashima et al. "Paired Termini Stabilize Antisense RNAs and Enhance Conditional Gene Silencing in *Escherichia coli*", Nucleic Acids Research, 34(20): e138-1-e138-10, Oct. 24, 2006.

* cited by examiner

*Primary Examiner* — Kevin Hill
(74) *Attorney, Agent, or Firm* — Wiggin and Dana LLP; Gregory S. Rosenblatt

(57) ABSTRACT

A genetically modified bacteriophage is disclosed which comprises:
  (i) an exogenous polynucleotide which encodes an agent which reduces the toxicity of a bacterium; and
  (ii) an exogenous polynucleotide which encodes a selectable marker.
Uses thereof and kits comprising same are also disclosed.

31 Claims, 8 Drawing Sheets

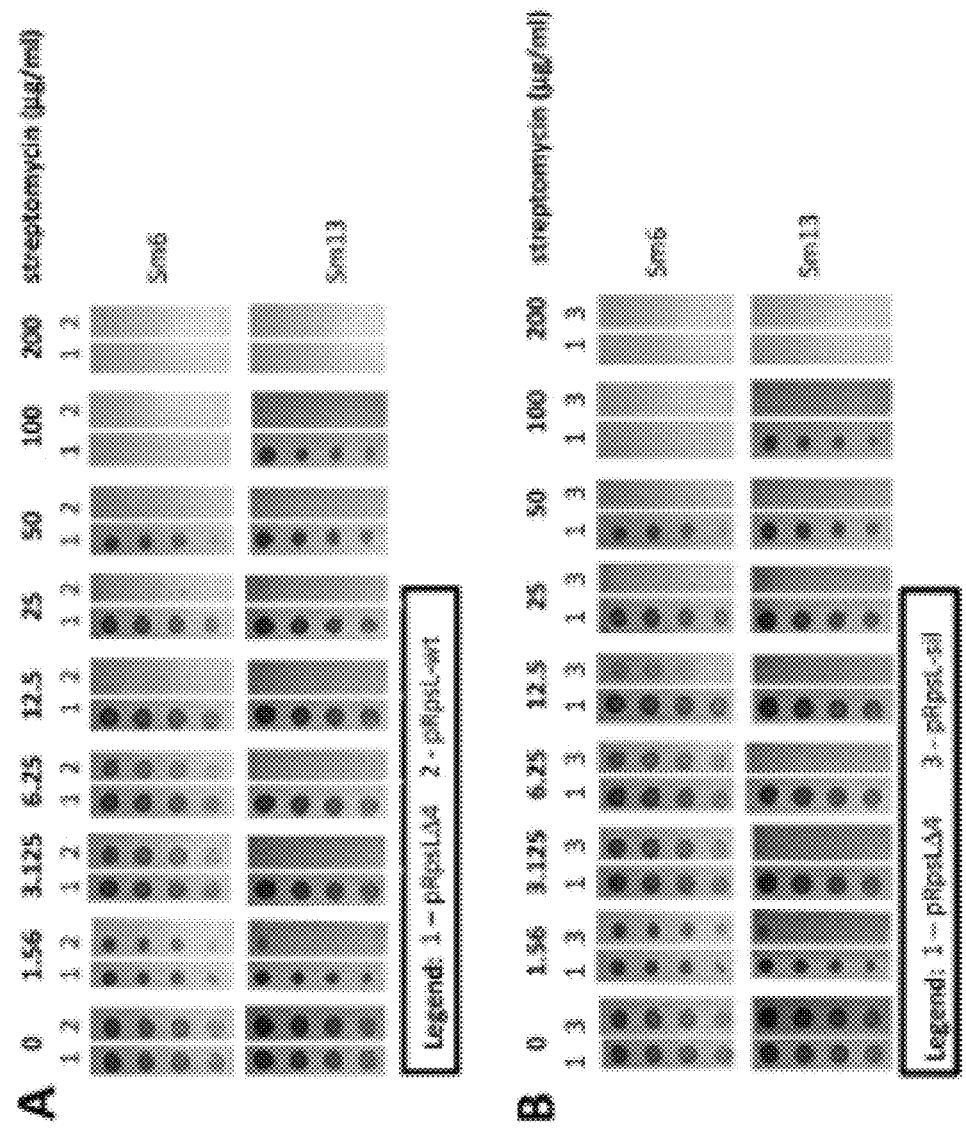
FIGs. 2A-B

FIGs. 4A-B

SEQUENCE LISTING

<160> NUMBER OF SEQ ID NOS: 32

<210> SEQ ID NO 1
<211> LENGTH: 74
<212> TYPE: DNA
<213> ORGANISM: Artificial sequence
<220> FEATURE:
<223> OTHER INFORMATION: Single strand DNA oligonucleotides

<400> SEQUENCE: 1
caataaccct gataaatgct tcaataatat tgaaaaagga agagtactag tatgcagagc        60
gataaagtgc tcaa        74

<210> SEQ ID NO 2
<211> LENGTH: 74

```
<212> TYPE: DNA
<213> ORGANISM: Artificial sequence
<220> FEATURE:
<223> OTHER INFORMATION: Single strand DNA oligonucleotides

<400> SEQUENCE: 2
aagttttaaa tcaatctaaa gtatatatga gtaaacttgg tctgacagct cgagtcattt    60
tttacgtgcc agca                                                     74

<210> SEQ ID NO 3
<211> LENGTH: 80
<212> TYPE: DNA
<213> ORGANISM: Artificial sequence
<220> FEATURE:
<223> OTHER INFORMATION: Single strand DNA oligonucleotides

<400> SEQUENCE: 3
tcgttttaca acgtcgtgga tccttaccaa tgcttaatca gtgaggctcg gattatcaaa    60
aaggatcttc acctagatcc                                               80

<210> SEQ ID NO 4
<211> LENGTH: 88
<212> TYPE: DNA
<213> ORGANISM: Artificial sequence
<220> FEATURE:
<223> OTHER INFORMATION: Single strand DNA oligonucleotides

<400> SEQUENCE: 4
acttaagctt aaaagagtat tgacttaaag tctaactata ggatacttac agccatagga    60
ggacagctat ggcaacagtt aaccagct                                      88

<210> SEQ ID NO 5
<211> LENGTH: 30
<212> TYPE: DNA
<213> ORGANISM: Artificial sequence
<220> FEATURE:
<223> OTHER INFORMATION: Single strand DNA oligonucleotides

<400> SEQUENCE: 5
ttcggaattc ttaagcctta ggacgcttca                                    30

<210> SEQ ID NO 6
<211> LENGTH: 30
<212> TYPE: DNA
<213> ORGANISM: Artificial sequence
<220> FEATURE:
<223> OTHER INFORMATION: Single strand DNA oligonucleotides

<400> SEQUENCE: 6
gctagaattc ggcgacggct tcaaatttag                                    30

<210> SEQ ID NO 7
<211> LENGTH: 27
<212> TYPE: DNA
<213> ORGANISM: Artificial sequence
<220> FEATURE:
<223> OTHER INFORMATION: Single strand DNA oligonucleotides

<400> SEQUENCE: 7
catatgttat tcttcttctg gctcgtc                                       27

<210> SEQ ID NO 8
<211> LENGTH: 30
<212> TYPE: DNA
```

-continued

<213> ORGANISM: Artificial sequence
<220> FEATURE:
<223> OTHER INFORMATION: Single strand DNA oligonucleotides

<400> SEQUENCE: 8
actttctaga aggaaacagc tatgaccatg                                           30

<210> SEQ ID NO 9
<211> LENGTH: 30
<212> TYPE: DNA
<213> ORGANISM: Artificial sequence
<220> FEATURE:
<223> OTHER INFORMATION: Single strand DNA oligonucleotides

<400> SEQUENCE: 9
taacggatcc ttaccaatgc ttaatcagtg                                           30

<210> SEQ ID NO 10
<211> LENGTH: 30
<212> TYPE: DNA
<213> ORGANISM: Artificial sequence
<220> FEATURE:
<223> OTHER INFORMATION: Single strand DNA oligonucleotides

<400> SEQUENCE: 10
taacggatcc acgacgttgt aaaacgacgg                                           30

<210> SEQ ID NO 11
<211> LENGTH: 30
<212> TYPE: DNA
<213> ORGANISM: Artificial sequence
<220> FEATURE:
<223> OTHER INFORMATION: Single strand DNA oligonucleotides

<400> SEQUENCE: 11
actttctaga aggtgaagat cctttttgat                                           30

<210> SEQ ID NO 12
<211> LENGTH: 30
<212> TYPE: DNA
<213> ORGANISM: Artificial sequence
<220> FEATURE:
<223> OTHER INFORMATION: Single strand DNA oligonucleotides

<400> SEQUENCE: 12
acgccaattg gtatgttgtg tggaattgtg                                           30

<210> SEQ ID NO 13
<211> LENGTH: 30
<212> TYPE: DNA
<213> ORGANISM: Artificial sequence
<220> FEATURE:
<223> OTHER INFORMATION: Single strand DNA oligonucleotides

<400> SEQUENCE: 13
cgttcaattg gttaagggat tttggtcatg                                           30

<210> SEQ ID NO 14
<211> LENGTH: 20
<212> TYPE: DNA
<213> ORGANISM: Artificial sequence
<220> FEATURE:
<223> OTHER INFORMATION: Single strand DNA oligonucleotides

<400> SEQUENCE: 14
cagacatgta taccccgtac                                                      20

<210> SEQ ID NO 15
<211> LENGTH: 20
<212> TYPE: DNA
<213> ORGANISM: Artificial sequence
<220> FEATURE:
<223> OTHER INFORMATION: Single strand DNA oligonucleotides

<400> SEQUENCE: 15
tacgccatgg ccggagtggc                                                    20

<210> SEQ ID NO 16
<211> LENGTH: 20
<212> TYPE: DNA
<213> ORGANISM: Artificial sequence
<220> FEATURE:
<223> OTHER INFORMATION: Single strand DNA oligonucleotides

<400> SEQUENCE: 16
gtgtgaaatt gttatccgct                                                    20

<210> SEQ ID NO 17
<211> LENGTH: 34
<212> TYPE: DNA
<213> ORGANISM: Artificial sequence
<220> FEATURE:
<223> OTHER INFORMATION: Single strand DNA oligonucleotides

<400> SEQUENCE: 17
actgactagt actcttcctt tttcaatatt attg                                    34

<210> SEQ ID NO 18
<211> LENGTH: 40
<212> TYPE: DNA
<213> ORGANISM: Artificial sequence
<220> FEATURE:
<223> OTHER INFORMATION: Single strand DNA oligonucleotides

<400> SEQUENCE: 18
ctgtcagacc aagtttactc ctgtcagacc aagtttactc                              40

<210> SEQ ID NO 19
<211> LENGTH: 30
<212> TYPE: DNA
<213> ORGANISM: Artificial sequence
<220> FEATURE:
<223> OTHER INFORMATION: Single strand DNA oligonucleotides

<400> SEQUENCE: 19
actgactagt atggagaaaa aaatcactgg                                         30

<210> SEQ ID NO 20
<211> LENGTH: 31
<212> TYPE: DNA
<213> ORGANISM: Artificial sequence
<220> FEATURE:
<223> OTHER INFORMATION: Single strand DNA oligonucleotides

<400> SEQUENCE: 20
ttcactcgag ttacgccccg ccctgccact c                                       31

<210> SEQ ID NO 21
<211> LENGTH: 47
<212> TYPE: DNA
<213> ORGANISM: Artificial sequence
<220> FEATURE:

<223> OTHER INFORMATION: Single strand DNA oligonucleotides

<400> SEQUENCE: 21
aaaagagtat tgacttaaag tctaacctat aggatactta cagccat                47

<210> SEQ ID NO 22
<211> LENGTH: 46
<212> TYPE: DNA
<213> ORGANISM: Artificial sequence
<220> FEATURE:
<223> OTHER INFORMATION: Single strand DNA oligonucleotides

<400> SEQUENCE: 22
aaaagagtat tgacttaaag tctaactata ggatacttac agccat                 46

<210> SEQ ID NO 23
<211> LENGTH: 375
<212> TYPE: DNA
<213> ORGANISM: Artificial sequence
<220> FEATURE:
<223> OTHER INFORMATION: E. Coli derived wildtype rpsL

<400> SEQUENCE: 23
atggcaacag ttaaccagct ggtacgcaaa ccacgtgctc gcaaagttgc gaaaagcaac      60
gtgcctgcgc tggaagcatg cccgcaaaaa cgtggcgtat gtactcgtgt atatactacc    120
actcctaaaa aaccgaactc cgcgctgcgt aaagtatgcc gtgttcgtct gactaacggt    180
ttcgaagtga cttcctacat cggtggtgaa ggtcacaacc tgcaggagca ctccgtgatc    240
ctgatccgtg gcggtcgtgt taaagacctc ccgggtgttc gttaccacac cgtacgtggt    300
gcgcttgact gctccggcgt taaagaccgt aagcaggctc gttccaagta tggcgtgaag    360
cgtcctaagg cttaa                                                     375

<210> SEQ ID NO 24
<211> LENGTH: 375
<212> TYPE: DNA
<213> ORGANISM: Artificial sequence
<220> FEATURE:
<223> OTHER INFORMATION: An exemplary polynucleotide sequence encoding
      wild-type 30S ribosomal subunit protein S12 (RpsL), modified so as
      to prevent homologous recombination

<400> SEQUENCE: 24
atggcgaccg tgaatcaatt agtgcgtaag ccgcgcgcgc gtaaggtggc aaagtcgaat      60
gttccggcct tagaggcgtg tccacagaag cgcggtgtgt gcacccgcgt gtacaccacg    120
accccgaaga agccaaatag tgccttacgc aaggtgtgtc gcgtgcgctt aacgaatggc    180
tttgaggtta ccagttatat tggcggcgag ggccataatt tacaagaaca tagtgttatt    240
ttaattcgcg gtggccgcgt gaaggatttg ccaggcgtgc gctatcatac ggtgcgcggc    300
gccttggatt gtagtggtgt gaaggatcgc aaacaagcgc gcagtaaata cggtgttaaa    360
cgcccgaaag cgtga                                                     375

<210> SEQ ID NO 25
<211> LENGTH: 124
<212> TYPE: PRT
<213> ORGANISM: Artificial sequence
<220> FEATURE:
<223> OTHER INFORMATION: RPSL wild-type amino acid sequence

<400> SEQUENCE: 25

Met Ala Thr Val Asn Gln Leu Val Arg Lys Pro Arg Ala Arg Lys Val

```
  1               5                  10                 15
Ala Lys Ser Asn Val Pro Ala Leu Glu Ala Cys Pro Gln Lys Arg Gly
                 20                 25                 30

Val Cys Thr Arg Val Tyr Thr Thr Thr Pro Lys Pro Asn Ser Ala
         35                 40                 45

Leu Arg Lys Val Cys Arg Val Arg Leu Thr Asn Gly Phe Glu Val Thr
 50                 55                 60

Ser Tyr Ile Gly Gly Glu Gly His Asn Leu Gln Glu His Ser Val Ile
 65                 70                 75                 80

Leu Ile Arg Gly Gly Arg Val Lys Asp Leu Pro Gly Val Arg Tyr His
                 85                 90                 95

Thr Val Arg Gly Ala Leu Asp Cys Ser Gly Val Lys Asp Arg Lys Gln
                100                105                110

Ala Arg Ser Lys Tyr Gly Val Lys Arg Pro Lys Ala
                115                120

<210> SEQ ID NO 26
<211> LENGTH: 2628
<212> TYPE: DNA
<213> ORGANISM: Artificial sequence
<220> FEATURE:
<223> OTHER INFORMATION: E. coli derived gyrA coding sequence

<400> SEQUENCE: 26
atgagcgacc ttgcgagaga aattacaccg gtcaacattg aggaagagct gaagagctcc      60
tatctggatt atgcgatgtc ggtcattgtt ggccgtgcgc tgccagatgt ccgagatggc     120
ctgaagccgg tacaccgtcg cgtactttac gccatgaacg tactaggcaa tgactggaac     180
aaagcctata aaaatctgc ccgtgtcgtt ggtgacgtaa tcggtaaata ccatccccat     240
ggtgactcgg cggtctatga cacgatcgtc cgcatggcgc agccattctc gctgcgttat     300
atgctggtag acggtcaggg taacttcggt tctatcgacg cgactctgc ggcggcaatg     360 cgttatacgg aaatccgtct ggcgaaaatt gcccatgaac tgatggccga tctcgaaaaa     420
gagacggtcg atttcgttga taactatgac ggcacggaaa aaattccgga cgtcatgcca     480
accaaaattc ctaacctgct ggtgaacggt tcttccggta tcgccgtagg tatggcaacc     540
aacatcccgc cgcacaacct gacggaagtc atcaacggtt gtctggcgta tattgatgat     600
gaagacatca gcattgaagg gctgatggaa cacatcccgg ggccggactt cccgacggcg     660
gcaatcatta acggtcgtcg cggtattgaa gaagcttacc gtaccggtcg cggcaaggtg     720
tatatccgcg ctcgcgcaga agtggaagtt gacgccaaaa ccggtcgtga accattatc     780 gtccacgaaa ttccgtatca ggtaaacaaa gcgcgcctga tcgagaagat gcggaactg     840 gtaaagaaa acgcgtgga aggcatcagc gcgctgcgtg acgagtctga caaagacggt     900
atgcgcatcg tgattgaagt gaaacgcgat gcggtcggtg aagttgtgct caacaacctc     960
tactcccaga cccagttgca ggtttctttc ggtatcaaca tggtggcatt gcaccatggt    1020
cagccgaaga tcatgaacct gaaagacatc atcgcggcgt tgttcgtca ccgccgtgaa    1080 gtggtgaccc gtcgtactat tttcgaactg cgtaaagctc gcgatcgtgc tcatatcctt    1140
gaagcattag ccgtggcgct ggcgaacatc gacccgatca tcgaactgat ccgtcatgcg    1200
ccgacgcctg cagaagcgaa aactgcgctg gttgctaatc cgtggcagct gggcaacgtt    1260
gccgcgatgc tcgaacgtgc tggcgacgat gctgcgcgtc cggaatggct ggagccagag    1320
ttcggcgtgc gtgatggtct gtactacctg accgaacagc aagctcaggc gattctggat    1380
```

```
ctgcgtttgc agaaactgac cggtcttgag cacgaaaaac tgctcgacga atacaaagag    1440
ctgctggatc agatcgcgga actgttgcgt attcttggta gcgccgatcg tctgatggaa    1500
gtgatccgtg aagagctgga gctggttcgt gaacagttcg gtgacaaacg tcgtactgaa    1560
atcaccgcca acagcgcaga catcaacctg gaagatctga tcacccagga agatgtggtc    1620
gtgacgctct ctcaccaggg ctacgttaag tatcagccgc tttctgaata cgaagcgcag    1680
cgtcgtggcg ggaaaggtaa atctgccgca cgtattaaag aagaagactt tatcgaccga    1740
ctgctggtgg cgaacactca cgaccatatt ctgtgcttct ccagccgtgg tcgcgtctat    1800
tcgatgaaag tttatcagtt gccggaagcc actcgtggcg cgcgcggtcg tccgatcgtc    1860
aacctgctgc cgctggagca ggacgaacgt atcactgcga tcctgccagt gaccgagttt    1920
gaagaaggcg tgaaagtctt catggcgacc gctaacggta ccgtgaagaa aactgtcctc    1980
accgagttca ccgtctgcg taccgccggt aaagtggcga tcaaactggt tgacggcgat    2040
gagctgatcg cgttgaccct gaccagcggc gaagacgaag taatgctgtt ctccgctgaa    2100
ggtaaagtgg tgcgctttaa agagtcttct gtccgtgcga tgggctgcaa caccaccggt    2160
gttcgcggta ttcgcttagg tgaaggcgat aaagtcgtct ctctgatcgt gcctcgtggc    2220
gatggcgcaa tcctcaccgc aacgcaaaac ggttacggta acgtaccgc agtggcggaa    2280 tacccaacca gtcgcgtgc gacgaaaggg gttatctcca tcaaggttac cgaacgtaac    2340
ggtttagttg ttggcgcggt acaggtagat gactgcgacc agatcatgat gatcaccgat    2400
gccggtacgc tggtacgtac tcgcgtttcg gaaatcagca tcgtgggccg taacacccag    2460
ggcgtgatcc tcatccgtac tgcggaagat gaaaacgtag tgggtctgca acgtgttgct    2520
gaaccggttg acgaggaaga tctggatacc atcgacggca gtgccgcgga aggggacgat    2580
gaaatcgctc cggaagtgga cgttgacgac gagccagaag aagaataa                2628
```

<210> SEQ ID NO 27
<211> LENGTH: 875
<212> TYPE: PRT
<213> ORGANISM: Artificial sequence
<220> FEATURE:
<223> OTHER INFORMATION: WT gyrase protein

<400> SEQUENCE: 27

```
Met Ser Asp Leu Ala Arg Glu Ile Thr Pro Val Asn Ile Glu Glu
1               5                   10                  15

Leu Lys Ser Ser Tyr Leu Asp Tyr Ala Met Ser Val Ile Val Gly Arg
            20                  25                  30

Ala Leu Pro Asp Val Arg Asp Gly Leu Lys Pro Val His Arg Arg Val
        35                  40                  45

Leu Tyr Ala Met Asn Val Leu Gly Asn Asp Trp Asn Lys Ala Tyr Lys
    50                  55                  60

Lys Ser Ala Arg Val Val Gly Asp Val Ile Gly Lys Tyr His Pro His
65                  70                  75                  80

Gly Asp Ser Ala Val Tyr Asp Thr Ile Val Arg Met Ala Gln Pro Phe
                85                  90                  95

Ser Leu Arg Tyr Met Leu Val Asp Gly Gln Gly Asn Phe Gly Ser Ile
            100                 105                 110

Asp Gly Asp Ser Ala Ala Ala Met Arg Tyr Thr Glu Ile Arg Leu Ala
        115                 120                 125

Lys Ile Ala His Glu Leu Met Ala Asp Leu Glu Lys Glu Thr Val Asp
    130                 135                 140
```

```
Phe Val Asp Asn Tyr Asp Gly Thr Glu Lys Ile Pro Asp Val Met Pro
145                 150                 155                 160

Thr Lys Ile Pro Asn Leu Leu Val Asn Gly Ser Ser Gly Ile Ala Val
            165                 170                 175

Gly Met Ala Thr Asn Ile Pro Pro His Asn Leu Thr Glu Val Ile Asn
            180                 185                 190

Gly Cys Leu Ala Tyr Ile Asp Asp Glu Asp Ile Ser Ile Glu Gly Leu
            195                 200                 205

Met Glu His Ile Pro Gly Pro Asp Phe Pro Thr Ala Ala Ile Ile Asn
        210                 215                 220

Gly Arg Gly Ile Glu Glu Ala Tyr Arg Thr Gly Arg Gly Lys Val
225                 230                 235                 240

Tyr Ile Arg Ala Arg Ala Glu Val Glu Val Asp Ala Lys Thr Gly Arg
                245                 250                 255

Glu Thr Ile Ile Val His Glu Ile Pro Tyr Gln Val Asn Lys Ala Arg
            260                 265                 270

Leu Ile Glu Lys Ile Ala Glu Leu Val Lys Glu Lys Arg Val Glu Gly
            275                 280                 285

Ile Ser Ala Leu Arg Asp Glu Ser Asp Lys Asp Gly Met Arg Ile Val
290                 295                 300

Ile Glu Val Lys Arg Asp Ala Val Gly Glu Val Val Leu Asn Asn Leu
305                 310                 315                 320

Tyr Ser Gln Thr Gln Leu Gln Val Ser Phe Gly Ile Asn Met Val Ala
                325                 330                 335

Leu His His Gly Gln Pro Lys Ile Met Asn Leu Lys Asp Ile Ile Ala
            340                 345                 350

Ala Phe Val Arg His Arg Arg Glu Val Val Thr Arg Arg Thr Ile Phe
            355                 360                 365

Glu Leu Arg Lys Ala Arg Asp Arg Ala His Ile Leu Glu Ala Leu Ala
        370                 375                 380

Val Ala Leu Ala Asn Ile Asp Pro Ile Ile Glu Leu Ile Arg His Ala
385                 390                 395                 400

Pro Thr Pro Ala Glu Ala Lys Thr Ala Leu Val Ala Asn Pro Trp Gln
                405                 410                 415

Leu Gly Asn Val Ala Ala Met Leu Glu Arg Ala Gly Asp Asp Ala Ala
            420                 425                 430

Arg Pro Glu Trp Leu Glu Pro Glu Phe Gly Val Arg Asp Gly Leu Tyr
        435                 440                 445

Tyr Leu Thr Glu Gln Gln Ala Gln Ala Ile Leu Asp Leu Arg Leu Gln
450                 455                 460

Lys Leu Thr Gly Leu Glu His Glu Lys Leu Leu Asp Glu Tyr Lys Glu
465                 470                 475                 480

Leu Leu Asp Gln Ile Ala Glu Leu Leu Arg Ile Leu Gly Ser Ala Asp
                485                 490                 495

Arg Leu Met Glu Val Ile Arg Glu Glu Leu Glu Leu Val Arg Glu Gln
            500                 505                 510

Phe Gly Asp Lys Arg Arg Thr Glu Ile Thr Ala Asn Ser Ala Asp Ile
            515                 520                 525

Asn Leu Glu Asp Leu Ile Thr Gln Glu Asp Val Val Thr Leu Ser
        530                 535                 540

His Gln Gly Tyr Val Lys Tyr Gln Pro Leu Ser Glu Tyr Glu Ala Gln
545                 550                 555                 560

Arg Arg Gly Gly Lys Gly Lys Ser Ala Ala Arg Ile Lys Glu Glu Asp
```

```
                        565                 570                 575
Phe Ile Asp Arg Leu Leu Val Ala Asn Thr His Asp His Ile Leu Cys
                580                 585                 590
Phe Ser Ser Arg Gly Arg Val Tyr Ser Met Lys Val Tyr Gln Leu Pro
                595                 600                 605
Glu Ala Thr Arg Gly Ala Arg Gly Arg Pro Ile Val Asn Leu Leu Pro
                610                 615                 620
Leu Glu Gln Asp Glu Arg Ile Thr Ala Ile Leu Pro Val Thr Glu Phe
625                 630                 635                 640
Glu Glu Gly Val Lys Val Phe Met Ala Thr Ala Asn Gly Thr Val Lys
                645                 650                 655
Lys Thr Val Leu Thr Glu Phe Asn Arg Leu Arg Thr Ala Gly Lys Val
                660                 665                 670
Ala Ile Lys Leu Val Asp Gly Asp Glu Leu Ile Gly Val Asp Leu Thr
                675                 680                 685
Ser Gly Glu Asp Glu Val Met Leu Phe Ser Ala Glu Gly Lys Val Val
                690                 695                 700
Arg Phe Lys Glu Ser Ser Val Arg Ala Met Gly Cys Asn Thr Thr Gly
705                 710                 715                 720
Val Arg Gly Ile Arg Leu Gly Glu Gly Asp Lys Val Val Ser Leu Ile
                725                 730                 735
Val Pro Arg Gly Asp Gly Ala Ile Leu Thr Ala Thr Gln Asn Gly Tyr
                740                 745                 750
Gly Lys Arg Thr Ala Val Ala Glu Tyr Pro Thr Lys Ser Arg Ala Thr
                755                 760                 765
Lys Gly Val Ile Ser Ile Lys Val Thr Glu Arg Asn Gly Leu Val Val
770                 775                 780
Gly Ala Val Gln Val Asp Asp Cys Asp Gln Ile Met Met Ile Thr Asp
785                 790                 795                 800
Ala Gly Thr Leu Val Arg Thr Arg Val Ser Glu Ile Ser Ile Val Gly
                805                 810                 815
Arg Asn Thr Gln Gly Val Ile Leu Ile Arg Thr Ala Glu Asp Glu Asn
                820                 825                 830
Val Val Gly Leu Gln Arg Val Ala Glu Pro Val Asp Glu Glu Asp Leu
                835                 840                 845
Asp Thr Ile Asp Gly Ser Ala Glu Gly Asp Glu Ile Ala Pro
                850                 855                 860
Glu Val Asp Val Asp Asp Glu Pro Glu Glu Glu
865                 870                 875

<210> SEQ ID NO 28
<211> LENGTH: 4029
<212> TYPE: DNA
<213> ORGANISM: Artificial sequence
<220> FEATURE:
<223> OTHER INFORMATION: E. coli derived rpoB coding sequence

<400> SEQUENCE: 28
atggtttact cctataccga gaaaaaacgt attcgtaagg attttggtaa acgtccacaa     60
gttctggatg tacctatct cctttctatc cagcttgact cgtttcagaa atttatcgag    120
caagatcctg aagggcagta tggtctggaa gctgcttcc gttccgtatt cccgattcag    180
agctacagcg gtaattccga gctgcaatac gtcagctacc gccttggcga accggtgttt    240
gacgtccagg aatgtcaaat ccgtggcgtg acctattccg caccgctgcg cgttaaactg    300
```

```
cgtctggtga tctatgagcg cgaagcgccg gaaggcaccg taaaagacat taaagaacaa    360
gaagtctaca tgggcgaaat tccgctcatg acagacaacg gtacctttgt tatcaacggt    420
actgagcgtg ttatcgtttc ccagctgcac cgtagtccgg gcgtcttctt tgactccgac    480
aaaggtaaaa cccactcttc gggtaaagtg ctgtataacg cgcgtatcat cccttaccgt    540
ggttcctggc tggacttcga attcgatccg aaggacaacc tgttcgtacg tatcgaccgt    600
cgccgtaaac tgcctgcgac catcattctg cgcgccctga actacaccac agagcagatc    660
ctcgacctgt tctttgaaaa agttatcttt gaaatccgtg ataacaagct gcagatggaa    720
ctggtgccgg aacgcctgcg tggtgaaacc gcatcttttg acatcgaagc taacggtaaa    780
gtgtacgtag aaaaaggccg ccgtatcact gcgcgccaca ttcgccagct ggaaaaagac    840
gacgtcaaac tgatcgaagt cccggttgag tacatcgcag gtaaagtggt tgctaaagac    900
tatattgatg agtctaccgg cgagctgatc tgcgcagcga acatggagct gagcctggat    960
ctgctggcta agctgagcca gtctggtcac aagcgtatcg aaacgctgtt caccaacgat   1020
ctggatcacg gcccatatat ctctgaaacc ttacgtgtcg acccaactaa cgaccgtctg   1080
agcgcactgg tagaaatcta ccgcatgatg cgccctggcg agccgccgac tcgtgaagca   1140
gctgaaagcc tgttcgagaa cctgttcttc tccgaagacc gttatgactt gtctgcggtt   1200
ggtcgtatga gttcaaccg ttctctgctg cgcgaagaaa tcgaaggttc cggtatcctg   1260
agcaaagacg acatcattga tgttatgaaa aagctcatcg atatccgtaa cggtaaaggc   1320
gaagtcgatg atatcgacca cctcggcaac cgtcgtatcc gttccgttgg cgaaatggcg   1380
gaaaaccagt tccgcgttgg cctggtacgt gtagagcgtg cggtgaaaga gcgtctgtct   1440
ctgggcgatc tggataccct gatgccacag gatatgatca acgccaagcc gatttccgca   1500
gcagtgaaag agttcttcgg ttccagccag ctgtctcagt ttatggacca gaacaacccg   1560
ctgtctgaga ttacgcacaa acgtcgtatc tccgcactcg gcccaggcgg tctgacccgt   1620
gaacgtgcag gcttcgaagt tcgagacgta caccgactc actacggtcg cgtatgtcca   1680
atcgaaaccc ctgaaggtcc gaacatcggt ctgatcaact ctctgtccgt gtacgcacag   1740
actaacgaat acggcttcct tgagactccg tatcgtaaag tgaccgacgg tgttgtaact   1800
gacgaaattc actacctgtc tgctatcgaa gaaggcaact acgttatcgc ccaggcgaac   1860
tccaacttgg atgaagaagg ccacttcgta gaagacctgg taacttgccg tagcaaaggc   1920
gaatccagct tgttcagccg cgaccaggtt gactacatgg acgtatccac ccagcaggtg   1980
gtatccgtcg gtgcgtccct gatcccgttc ctggaacacg atgacgccaa ccgtgcattg   2040
atgggtgcga acatgcaacg tcaggccgtt ccgactctgc gcgctgataa gccgctggtt   2100
ggtactggta tggaacgtgc tgttgccgtt gactccggtg taactgcggt agctaaacgt   2160
ggtggtgtcg ttcagtacgt ggatgcttcc cgtatcgtta tcaaagttaa cgaagacgag   2220
atgtatccgg gtgaagcagg tatcgacatc tacaacctga ccaaatacac ccgttctaac   2280 cagaacaccct gtatcaacca gatgccgtgt gtgtctctgg gtgaaccggt tgaacgtggc   2340
gacgtgctgg cagacggtcc gtccaccgac ctcggtgaac tggcgcttgg tcagaacatg   2400
cgcgtagcgt tcatgccgtg gaatggttac aacttcgaag actccatcct cgtatccgag   2460
cgtgttgttc aggaagaccg tttcaccacc atccacattc aggaactggc gtgtgtgtcc   2520
cgtgacacca gctgggtcc ggaagagatc accgctgaca tcccgaacgt gggtgaagct   2580
gcgctctcca aactgatga atccggtatc gtttacattg gtgcggaagt gaccggtggc   2640
gacattctgg ttggtaaggt aacgccgaaa ggtgaaactc agctgacccc agaagaaaaa   2700
```

-continued

```
ctgctgcgtg cgatcttcgg tgagaaagcc tctgacgtta aagactcttc tctgcgcgta    2760
ccaaacggtg tatccggtac ggttatcgac gttcaggtct ttactcgcga tggcgtagaa    2820
aaagacaaac gtgcgctgga atcgaagaa atgcagctca acaggcgaa gaaagacctg     2880 tctgaagaac tgcagatcct cgaagcgggt ctgttcagcc gtatccgtgc tgtgctggta    2940
gccggtggcg ttgaagctga aagctcgac aaactgccgc gcgatcgctg gctggagctg     3000
ggcctgacag acgaagagaa acaaaatcag ctggaacagc tggctgagca gtatgacgaa    3060
ctgaaacacg agttcgagaa gaaactcgaa gcgaaacgcc gcaaaatcac ccagggcgac    3120
gatctggcac cggcgtgct gaagattgtt aaggtatatc tggcggttaa cgccgtatc      3180 cagcctggtg acaagatggc aggtcgtcac ggtaacaagg gtgtaatttc taagatcaac    3240
ccgatcgaag atatgcctta cgatgaaaac ggtacgccgg tagacatcgt actgaacccg    3300
ctgggcgtac cgtctcgtat gaacatcggt cagatcctcg aaacccacct gggtatggct    3360
gcgaaaggta tcggcgacaa gatcaacgcc atgctgaaac agcagcaaga agtcgcgaaa    3420
ctgcgcgaat tcatccagcg tgcgtacgat ctgggcgctg acgttcgtca gaaagttgac    3480
ctgagtacct tcagcgatga agaagttatg cgtctggctg aaaacctgcg caaaggtatg    3540
ccaatcgcaa cgccggtgtt cgacggtgcg aaagaagcag aaattaaaga gctgctgaaa    3600
cttggcgacc tgccgacttc cggtcagatc cgcctgtacg atggtcgcac tggtgaacag    3660
ttcgagcgtc cggtaaccgt tggttacatg tacatgctga aactgaacca cctggtcgac    3720
gacaagatgc acgcgcgttc caccggttct tacagcctgg ttactcagca gccgctgggt    3780
ggtaaggcac agttcggtgg tcagcgtttc ggggagatgg aagtgtgggc gctggaagca    3840
tacggcgcag catacaccct gcaggaaatg ctcaccgtta gtctgatga cgtgaacggt      3900 cgtaccaaga tgtataaaaa catcgtggac ggcaaccatc agatggagcc gggcatgcca    3960
gaatccttca acgtattgtt gaaagagatt cgttcgctgg gtatcaacat cgaactggaa    4020
gacgagtaa                                                            4029
```

<210> SEQ ID NO 29
<211> LENGTH: 1282
<212> TYPE: PRT
<213> ORGANISM: Artificial sequence
<220> FEATURE:
<223> OTHER INFORMATION: WT RNA Polymerase Beta

<400> SEQUENCE: 29

```
Ser Tyr Ser Gly Asn Ser Glu Leu Gln Tyr Val Ser Tyr Arg Leu Gly
1               5                   10                  15

Glu Pro Val Phe Asp Val Gln Glu Cys Gln Ile Arg Gly Val Thr Tyr
            20                  25                  30

Ser Ala Pro Leu Arg Val Lys Leu Arg Leu Val Ile Tyr Glu Arg Glu
        35                  40                  45

Ala Pro Glu Gly Thr Val Lys Asp Ile Lys Gln Glu Val Tyr Met
    50                  55                  60

Gly Glu Ile Pro Leu Met Thr Asp Asn Gly Thr Phe Val Ile Asn Gly
65                  70                  75                  80

Thr Glu Arg Val Ile Val Ser Gln Leu His Arg Ser Pro Gly Val Phe
                85                  90                  95

Phe Asp Ser Asp Lys Gly Lys Thr His Ser Ser Gly Lys Val Leu Tyr
            100                 105                 110

Asn Ala Arg Ile Ile Pro Tyr Arg Gly Ser Trp Leu Asp Phe Glu Phe
```

```
            115                 120                 125
Asp Pro Lys Asp Asn Leu Phe Val Arg Ile Asp Arg Arg Lys Leu
    130                 135                 140
Pro Ala Thr Ile Ile Leu Arg Ala Leu Asn Tyr Thr Thr Glu Gln Ile
145                 150                 155                 160
Leu Asp Leu Phe Phe Glu Lys Val Ile Phe Glu Ile Arg Asp Asn Lys
                    165                 170                 175
Leu Gln Met Glu Leu Val Pro Glu Arg Leu Arg Gly Glu Thr Ala Ser
                180                 185                 190
Phe Asp Ile Glu Ala Asn Gly Lys Val Tyr Val Glu Lys Gly Arg Arg
                195                 200                 205
Ile Thr Ala Arg His Ile Arg Gln Leu Glu Lys Asp Asp Val Lys Leu
            210                 215                 220
Ile Glu Val Pro Val Glu Tyr Ile Ala Gly Lys Val Val Ala Lys Asp
225                 230                 235                 240
Tyr Ile Asp Glu Ser Thr Gly Glu Leu Ile Cys Ala Ala Asn Met Glu
                245                 250                 255
Leu Ser Leu Asp Leu Leu Ala Lys Leu Ser Gln Ser Gly His Lys Arg
                260                 265                 270
Ile Glu Thr Leu Phe Thr Asn Asp Leu Asp His Gly Pro Tyr Ile Ser
            275                 280                 285
Glu Thr Leu Arg Val Asp Pro Thr Asn Asp Arg Leu Ser Ala Leu Val
            290                 295                 300
Glu Ile Tyr Arg Met Met Arg Pro Gly Glu Pro Pro Thr Arg Glu Ala
305                 310                 315                 320
Ala Glu Ser Leu Phe Glu Asn Leu Phe Phe Ser Glu Asp Arg Tyr Asp
                325                 330                 335
Leu Ser Ala Val Gly Arg Met Lys Phe Asn Arg Ser Leu Leu Arg Glu
                340                 345                 350
Glu Ile Glu Gly Ser Gly Ile Leu Ser Lys Asp Asp Ile Ile Asp Val
            355                 360                 365
Met Lys Lys Leu Ile Asp Ile Arg Asn Gly Lys Gly Glu Val Asp Asp
    370                 375                 380
Ile Asp His Leu Gly Asn Arg Arg Ile Arg Ser Val Gly Glu Met Ala
385                 390                 395                 400
Glu Asn Gln Phe Arg Val Gly Leu Val Arg Val Glu Arg Ala Val Lys
                405                 410                 415
Glu Arg Leu Ser Leu Gly Asp Leu Asp Thr Leu Met Pro Gln Asp Met
                420                 425                 430
Ile Asn Ala Lys Pro Ile Ser Ala Ala Val Lys Glu Phe Phe Gly Ser
            435                 440                 445
Ser Gln Leu Ser Gln Phe Met Asp Gln Asn Asn Pro Leu Ser Glu Ile
            450                 455                 460
Thr His Lys Arg Arg Ile Ser Ala Leu Gly Pro Gly Gly Leu Thr Arg
465                 470                 475                 480
Glu Arg Ala Gly Phe Glu Val Arg Asp Val His Pro Thr His Tyr Gly
                485                 490                 495
Arg Val Cys Pro Ile Glu Thr Pro Glu Gly Pro Asn Ile Gly Leu Ile
                500                 505                 510
Asn Ser Leu Ser Val Tyr Ala Gln Thr Asn Glu Tyr Gly Phe Leu Glu
            515                 520                 525
Thr Pro Tyr Arg Lys Val Thr Asp Gly Val Val Thr Asp Glu Ile His
            530                 535                 540
```

```
Tyr Leu Ser Ala Ile Glu Glu Gly Asn Tyr Val Ile Ala Gln Ala Asn
545                 550                 555                 560

Ser Asn Leu Asp Glu Glu Gly His Phe Val Glu Asp Leu Val Thr Cys
                565                 570                 575

Arg Ser Lys Gly Glu Ser Ser Leu Phe Ser Arg Asp Gln Val Asp Tyr
            580                 585                 590

Met Asp Val Ser Thr Gln Gln Val Ser Val Gly Ala Ser Leu Ile
                595                 600                 605

Pro Phe Leu Glu His Asp Asp Ala Asn Arg Ala Leu Met Gly Ala Asn
610                 615                 620

Met Gln Arg Gln Ala Val Pro Thr Leu Arg Ala Asp Lys Pro Leu Val
625                 630                 635                 640

Gly Thr Gly Met Glu Arg Ala Val Ala Val Asp Ser Gly Val Thr Ala
                645                 650                 655

Val Ala Lys Arg Gly Val Val Gln Tyr Val Asp Ala Ser Arg Ile
            660                 665                 670

Val Ile Lys Val Asn Glu Asp Glu Met Tyr Pro Gly Glu Ala Gly Ile
            675                 680                 685

Asp Ile Tyr Asn Leu Thr Lys Tyr Thr Arg Ser Asn Gln Asn Thr Cys
690                 695                 700

Ile Asn Gln Met Pro Cys Val Ser Leu Gly Glu Pro Val Glu Arg Gly
705                 710                 715                 720

Asp Val Leu Ala Asp Gly Pro Ser Thr Asp Leu Gly Glu Leu Ala Leu
                725                 730                 735

Gly Gln Asn Met Arg Val Ala Phe Met Pro Trp Asn Gly Tyr Asn Phe
                740                 745                 750

Glu Asp Ser Ile Leu Val Ser Glu Arg Val Val Gln Asp Arg Phe
            755                 760                 765

Thr Thr Ile His Ile Gln Glu Leu Ala Cys Val Ser Arg Asp Thr Lys
                770                 775                 780

Leu Gly Pro Glu Glu Ile Thr Ala Asp Ile Pro Asn Val Gly Glu Ala
785                 790                 795                 800

Ala Leu Ser Lys Leu Asp Glu Ser Gly Ile Val Tyr Ile Gly Ala Glu
                805                 810                 815

Val Thr Gly Gly Asp Ile Leu Val Gly Lys Val Thr Pro Lys Gly Glu
                820                 825                 830

Thr Gln Leu Thr Pro Glu Glu Lys Leu Leu Arg Ala Ile Phe Gly Glu
                835                 840                 845

Lys Ala Ser Asp Val Lys Asp Ser Ser Leu Arg Val Pro Asn Gly Val
850                 855                 860

Ser Gly Thr Val Ile Asp Val Gln Val Phe Thr Arg Asp Gly Val Glu
865                 870                 875                 880

Lys Asp Lys Arg Ala Leu Glu Ile Glu Glu Met Gln Leu Lys Gln Ala
                885                 890                 895

Lys Lys Asp Leu Ser Glu Glu Leu Gln Ile Leu Glu Ala Gly Leu Phe
            900                 905                 910

Ser Arg Ile Arg Ala Val Leu Val Ala Gly Gly Val Glu Ala Glu Lys
            915                 920                 925

Leu Asp Lys Leu Pro Arg Asp Arg Trp Leu Glu Leu Gly Leu Thr Asp
930                 935                 940

Glu Glu Lys Gln Asn Gln Leu Glu Gln Leu Ala Glu Gln Tyr Asp Glu
945                 950                 955                 960
```

| | | | | | | | | | | | |
|---|---|---|---|---|---|---|---|---|---|---|---|
|Leu|Lys|His|Glu|Phe|Glu|Lys|Lys|Leu|Glu|Ala|Lys|Arg|Arg|Lys|Ile|
| | | |965| | | |970| | | |975|

Thr Gln Gly Asp Asp Leu Ala Pro Gly Val Leu Lys Ile Val Lys Val
              980                985                990

Tyr Leu Ala Val Lys Arg Arg Ile Gln Pro Gly Asp Lys Met Ala Gly
        995                1000                1005

Arg His Gly Asn Lys Gly Val Ile Ser Lys Ile Asn Pro Ile Glu
    1010                1015                1020

Asp Met Pro Tyr Asp Glu Asn Gly Thr Pro Val Asp Ile Val Leu
    1025                1030                1035

Asn Pro Leu Gly Val Pro Ser Arg Met Asn Ile Gly Gln Ile Leu
    1040                1045                1050

Glu Thr His Leu Gly Met Ala Ala Lys Gly Ile Gly Asp Lys Ile
    1055                1060                1065

Asn Ala Met Leu Lys Gln Gln Gln Val Ala Lys Leu Arg Glu
    1070                1075                1080

Phe Ile Gln Arg Ala Tyr Asp Leu Gly Ala Asp Val Arg Gln Lys
    1085                1090                1095

Val Asp Leu Ser Thr Phe Ser Asp Glu Glu Val Met Arg Leu Ala
    1100                1105                1110

Glu Asn Leu Arg Lys Gly Met Pro Ile Ala Thr Pro Val Phe Asp
    1115                1120                1125

Gly Ala Lys Glu Ala Glu Ile Lys Glu Leu Leu Lys Leu Gly Asp
    1130                1135                1140

Leu Pro Thr Ser Gly Gln Ile Arg Leu Tyr Asp Gly Arg Thr Gly
    1145                1150                1155

Glu Gln Phe Glu Arg Pro Val Thr Val Gly Tyr Met Tyr Met Leu
    1160                1165                1170

Lys Leu Asn His Leu Val Asp Asp Lys Met His Ala Arg Ser Thr
    1175                1180                1185

Gly Ser Tyr Ser Leu Val Thr Gln Gln Pro Leu Gly Gly Lys Ala
    1190                1195                1200

Gln Phe Gly Gly Gln Arg Phe Gly Glu Met Glu Val Trp Ala Leu
    1205                1210                1215

Glu Ala Tyr Gly Ala Ala Tyr Thr Leu Gln Glu Met Leu Thr Val
    1220                1225                1230

Lys Ser Asp Asp Val Asn Gly Arg Thr Lys Met Tyr Lys Asn Ile
    1235                1240                1245

Val Asp Gly Asn His Gln Met Glu Pro Gly Met Pro Glu Ser Phe
    1250                1255                1260

Asn Val Leu Leu Lys Glu Ile Arg Ser Leu Gly Ile Asn Ile Glu
    1265                1270                1275

Leu Glu Asp Glu
    1280

<210> SEQ ID NO 30
<211> LENGTH: 795
<212> TYPE: DNA
<213> ORGANISM: Artificial sequence
<220> FEATURE:
<223> OTHER INFORMATION: E. coli derived thyA coding sequence

<400> SEQUENCE: 30
atgaaacagt atttagaact gatgcaaaaa gtgctcgacg aaggcacaca gaaaaacgac    60
cgtaccggaa ccggaacgct ttccattttt ggtcatcaga tgcgttttaa cctgcaagat   120

```
ggattcccgc tggtgacaac taaacgttgc cacctgcgtt ccatcatcca tgaactgctg       180
tggtttctgc agggcgacac taacattgct tatctacacg aaaacaatgt caccatctgg       240
gacgaatggg ccgatgaaaa cggcgacctc gggccagtgt atggtaaaca gtggcgcgcc       300
tggccaacgc cagatggtcg tcatattgac cagatcacta cggtactgaa ccagctgaaa       360
aacgacccgg attcgcgccg cattattgtt tcagcgtgga acgtaggcga actggataaa       420
atggcgctgg caccgtgcca tgcattcttc cagttctatg tggcagacgg caaactctct       480
tgccagcttt atcagcgctc ctgtgacgtc ttcctcggcc tgccgttcaa cattgccagc       540
tacgcgttat tggtgcatat gatggcgcag cagtgcgatc tggaagtggg tgattttgtc       600
tggaccggtg gcgacacgca tctgtacagc aaccatatgg atcaaactca tctgcaatta       660
agccgcgaac gcgtccgct gccgaagttg attatcaaac gtaaaccgga atccatcttc       720
gactaccgtt tcgaagactt tgagattgaa ggctacgatc gcatcccggg cattaaagcg       780
ccggtggcta tctaa                                                        795
```

```
<210> SEQ ID NO 31
<211> LENGTH: 264
<212> TYPE: PRT
<213> ORGANISM: Artificial sequence
<220> FEATURE:
<223> OTHER INFORMATION: WT thymidylate synthase

<400> SEQUENCE: 31
```

```
Met Lys Gln Tyr Leu Glu Leu Met Gln Lys Val Leu Asp Glu Gly Thr
1               5                   10                  15

Gln Lys Asn Asp Arg Thr Gly Thr Gly Thr Leu Ser Ile Phe Gly His
            20                  25                  30

Gln Met Arg Phe Asn Leu Gln Asp Gly Phe Pro Leu Val Thr Thr Lys
        35                  40                  45

Arg Cys His Leu Arg Ser Ile Ile His Glu Leu Leu Trp Phe Leu Gln
    50                  55                  60

Gly Asp Thr Asn Ile Ala Tyr Leu His Glu Asn Asn Val Thr Ile Trp
65                  70                  75                  80

Asp Glu Trp Ala Asp Glu Asn Gly Asp Leu Gly Pro Val Tyr Gly Lys
                85                  90                  95

Gln Trp Arg Ala Trp Pro Thr Pro Asp Gly Arg His Ile Asp Gln Ile
            100                 105                 110

Thr Thr Val Leu Asn Gln Leu Lys Asn Asp Pro Asp Ser Arg Arg Ile
        115                 120                 125

Ile Val Ser Ala Trp Asn Val Gly Glu Leu Asp Lys Met Ala Leu Ala
    130                 135                 140

Pro Cys His Ala Phe Phe Gln Phe Tyr Val Ala Asp Gly Lys Leu Ser
145                 150                 155                 160

Cys Gln Leu Tyr Gln Arg Ser Cys Asp Val Phe Leu Gly Leu Pro Phe
                165                 170                 175

Asn Ile Ala Ser Tyr Ala Leu Leu Val His Met Met Ala Gln Gln Cys
            180                 185                 190

Asp Leu Glu Val Gly Asp Phe Val Trp Thr Gly Gly Asp Thr His Leu
        195                 200                 205

Tyr Ser Asn His Met Asp Gln Thr His Leu Gln Leu Ser Arg Glu Pro
    210                 215                 220

Arg Pro Leu Pro Lys Leu Ile Ile Lys Arg Lys Pro Glu Ser Ile Phe
225                 230                 235                 240
```

```
Asp Tyr Arg Phe Glu Asp Phe Glu Ile Glu Gly Tyr Asp Pro His Pro
            245                 250                 255

Gly Ile Lys Ala Pro Val Ala Ile
        260

<210> SEQ ID NO 32
<211> LENGTH: 1583
<212> TYPE: DNA
<213> ORGANISM: Artificial sequence
<220> FEATURE:
<223> OTHER INFORMATION: tehA/B operon

<400> SEQUENCE: 32
atgcagagcg ataaagtgct caatttgccg gcaggctact ttggtattgt gttggggacg      60 ataggggatgg gatttgcctg gcgctatgcc agccaggttt gcaggtcag ccactggtta     120 ggggatgggc tggtgattct ggcgatgatc atctggggat tattgactag cgcatttatt    180
gcccgactca tacgctttcc gcatagcgtg ctggcggaag ttcgccatcc agtgctgagc    240
agttttgtga gtttgtttcc ggcaacgacg atgctggtgg cgattggttt tgttccgtgg    300
tttcgcccac tggcggtgtg cctgttcagt tttggtgtcg tggttcagtt ggcttatgcc    360
gcctggcaaa ctgcgggatt atggcgcgga tctcaccctg aagaagctac cacgcctgga    420
ctgtatctgc cgacagttgc caacaacttt atcagcgcaa tggcctgtgg tgcgttgggc    480
tacaccgacg ccggtctggt gtttttaggc gcaggcgttt tctcatggct aagccttgaa    540
ccggtgatct tgcagcgtct gcgcagttcg ggagaattac ccacggcact gcggacatca    600
ctcggcattc agctcgctcc tgcgctggtg gcttgtagtg cctggctgag cgtcaacggc    660
ggcgagggtg acacgctggc gaaaatgctt ttcggttatg gactgctgca actgctgttt    720
atgctacgtc tgatgccatg gtatctctcc cagccatttta atgcttcatt ctggagtttc    780
tcgttcggcg tatctgcact ggcaaccacc ggtttgcatc tggggagtgg cagcgataat    840
ggatttttcc atacgctggc ggtgccgctg tttatcttta ccaatttat tattgcaata    900 ctgctcatcc gtacttttgc gcttctgatg cagggaaaat tgttagtcag aaccgagcgc    960
gccgttttaa tgaaagcaga ggacaaagaa tgatcattcg tgacgaaaac tattttactg   1020
ataaatatga attaacccgc acacactctg aagtactgga agcggtgaaa gtggttaaac   1080
cgggtaaaac gctggatctg ggctgtggca atggtcgtaa cagtctttac ctggcagcca   1140
atggttatga tgttgacgca tgggataaaa atgccatgag tatcgccaac gtcgagcgca   1200
ttaaatccat tgaaaatctg ataatttac acacccgagt cgttgatctg aataacctca   1260
catttgatag acagtacgat tttattcttt cgactgtggt gctgatgttc cttgaggcta   1320
aaaccatccc cgggttgatt gccaatatgc aacgttgcac taaacctggt ggttacaacc   1380
tgattgtggc ggcgatggat accgctgatt atccatgtac cgtcggcttc ccgtttgcct   1440
tcaaagaggg agaattacgt cgatattacg aaggctggga gagggtgaaa tacaatgaag   1500
acgtcggcga gctgcaccgc accgacgcca acggtaatcg tattaaactg cgtttcgcca   1560
cgatgctggc acgtaaaaaa tga                                            1583
```

BACTERIOPHAGES FOR REDUCING TOXICITY OF BACTERIA

FIELD AND BACKGROUND OF THE INVENTION

The present invention, in some embodiments thereof, relates to a method of reducing toxicity of bacteria and more particularly reducing antibiotic resistance in bacteria.

Bacteria have evolved to overcome a wide range of antibiotics, and resistance mechanisms against most of the conventional antibiotics have been identified in some bacteria. Accelerated development of newer antibiotics is being overrun by the pace of bacterial resistance. In the USA, for example, over 70% of hospital-acquired infections involve bacteria resistant to at least one antibiotic, and in Japan over 50% of the clinical isolates of *Staphylococcus aureus* are multidrug-resistant.

This increasing threat has revived research into phage therapy. For example, a clinical phase I and II control trial was recently completed successfully for the treatment of chronic bacterial ear infections. Nevertheless, although phage therapy has been practiced for several decades in some of the former Soviet Union countries and Poland, there are still many doubts as to its ability to replace antibiotics. Major concerns over the use of phage therapy include neutralization of phages by the spleen/liver and by the immune system, their narrow host range, bacterial resistance to the phage, and lack of sufficient pharmacokinetic and efficacy studies in humans and animals.

A recent study used phages as a genetic tool to increase bacterial susceptibility to antibiotics. That study used phage M13, of the Gram-negative *Escherichia coli*, to genetically target several gene networks, thus rendering the bacteria more sensitive to antibiotics (10). It demonstrated that disrupting the SOS response by M13-mediated gene-targeting renders the bacteria several-fold more sensitive to a variety of antibiotics. It also demonstrated that phage-mediated gene transfer combined with antibiotics increases the survival of mice infected with pathogenic *E. coli*. Overall, the study showed that transferring genes by phage M13 weakens the bacteria, and render them more susceptible to killing by antibiotics. The end result is very similar to conventional phage-therapy practices, in which phages are used to directly kill the pathogen.

Different approaches make use of phages as "disinfectants" of pathogens present on edible foods, plants, and farm animals. In addition to increasing the shelf life of these products, the treatment is intended to prevent occasional outbreaks of disease. The US Food and Drug Administration recently approved the use of an anti-*Listeria* phage cocktail for application on meat and poultry as a preventive measure to against *Listeria* (5). Other phage cocktails have been approved as food additives in Europe, and many are currently being developed by phage biotech companies. These applications demonstrate that phages can be dispersed in the environment and efficiently target pathogens in their surroundings.

Pathogen resistance to antibiotics is a rapidly growing problem, leading to an urgent need for novel antimicrobial agents. Unfortunately, development of new antibiotics faces numerous obstacles, and a method that will resensitize pathogens to approved antibiotics therefore holds key advantages.

Lu and Collins [Proc Natl Acad Sci USA. 2009 Mar. 24; 106 (12):4629-34] teach genetically modified bacteriophage which serve to weaken bacteria such that they are more susceptible to antibiotics.

Hagens and Blassi [Lett Appl Microbiol. 2003; 37 (4):318-23] teach genetically modified filamentous phage as bactericidal agents.

Other background art includes U.S. Patent Application No. 20100322903 and Lederberg J., 1951, J Bacteriol 61:549-550 which teaches that wt rpsL is a dominant sensitive allele with regard to streptomycin resistance.

SUMMARY OF THE INVENTION

According to an aspect of some embodiments of the present invention there is provided a genetically modified bacteriophage comprising:

(i) an exogenous polynucleotide which encodes an agent which reduces the toxicity of a bacterium; and (ii) an exogenous polynucleotide which encodes a selectable marker.

According to an aspect of some embodiments of the present invention there is provided a kit comprising a compound which is toxic to bacteria and the phage of embodiments of the present invention, wherein the selectable marker renders a bacterium infected by the phage insensitive to the compound.

According to an aspect of some embodiments of the present invention there is provided a genetically modified bacteriophage comprising an exogenous polynucleotide which encodes a polypeptide which reverses resistance of a bacterium to an antibiotic, wherein the polypeptide is selected from the group consisting of 30S ribosomal subunit protein S12, gyrase, RNA Polymerase B Subunit and thymidylate synthase.

According to an aspect of some embodiments of the present invention there is provided an anti-bacterial composition, comprising a carrier and as an active ingredient the bacteriophage of embodiments of the present invention.

According to an aspect of some embodiments of the present invention there is provided an method of preventing a bacterial infection which is resistant to an antibiotic in a subject, the method comprising contacting a solid surface with the anti-bacterial composition described herein, thereby preventing the bacterial infection.

According to an aspect of some embodiments of the present invention there is provided an isolated population of bacterial cells comprising the bacteriophage of embodiments of the present invention.

According to some embodiments of the invention, the selectable marker is not an antibiotic resistance gene.

According to some embodiments of the invention, the agent reverses resistance of the bacterium to an antibiotic.

According to some embodiments of the invention, the resistance is due to a mutated polypeptide of the bacterium selected from the group consisting of 30S ribosomal subunit protein S12, gyrase, RNA Polymerase B Subunit and thymidylate synthase.

According to some embodiments of the invention, the agent is non-toxic to the bacterium.

According to some embodiments of the invention, the agent comprises a polypeptide selected from the group consisting of 30S ribosomal subunit protein S12, gyrase, RNA Polymerase β Subunit and thymidylate synthase.

According to some embodiments of the invention, the agent comprises a 30S ribosomal subunit protein S12.

According to some embodiments of the invention, the 30S ribosomal subunit protein S12 comprises a nucleic acid sequence as set forth in SEQ ID NO: 24.

According to some embodiments of the invention, the agent is a polynucleotide agent which down-regulates expression of an antibiotic resistance gene expressed in the bacterium.

According to some embodiments of the invention, the agent is a polynucleotide agent which down-regulates expression of a virulence gene expressed in the to bacterium.

According to some embodiments of the invention, the polynucleotide agent is selected from the group consisting of an siRNA, a short hairpin RNA, a ribozyme and a DNAzyme.

According to some embodiments of the invention, the polypeptide is non-toxic to the bacterium.

According to some embodiments of the invention, the polypeptide comprises a 30S ribosomal subunit protein S12.

According to some embodiments of the invention, the 30S ribosomal subunit protein S12 is encoded by a polynucleotide sequence as set forth in SEQ ID NO: 24.

According to some embodiments of the invention, the exogenous polynucleotide further encodes a selectable marker.

According to some embodiments of the invention, the selectable marker comprises a resistance marker to tellurite.

According to some embodiments of the invention, the bacteriophage is a lambda temperate phage.

According to some embodiments of the invention, the antibacterial composition is formulated as a spray, a stick, a paint, a gel, a cream, wash, a wipe, a foam, a soap, an oil, a solution, a lotion, an ointment or a paste.

According to some embodiments of the invention, the method further comprises contacting the solid surface with a compound which is toxic to bacteria.

According to some embodiments of the invention, the method further comprises contacting the solid surface with a compound which is toxic to bacteria.

According to some embodiments of the invention, the exogenous polynucleotide further encodes a selectable marker that renders a bacterium infected by the phage insensitive to the compound.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings.

T7-A1: AAAAGAGTATTGACTTAAAGTCTAACCTATAGGATACTTACAGCCAT (SEQ ID NO: 21,

T7-A1*: AAAAGAGTATTGACTTAAAGTCTAACTATAGGATACTTACAGCCAT (SEQ ID NO: 22;

rpsLΔ4—encodes a truncated RpsL protein, rpsL-wt—encodes the RpsL protein;

rpsL-sil—encodes an RpsL protein, harboring numerous silent mutations, with only 62% identity to the wt sequence; tehA/tehB—encode proteins which confer tellurite resistance; gyrA-wt—encodes the Gyrase A protein.

FIGS. 2A-B are photographs indicating that rpsL encoded by plasmids efficiently sensitizes streptomycin-resistant mutants. Streptomycin-resistant mutants Sm6 and Sm13, transformed with a plasmid encoding wt rpsL, pRpsL-wt (A) or rpsL having multiple silent mutations, pRpsL-sil (B), become more sensitive to streptomycin as compared to mutants transformed with a plasmid encoding a mock gene, pRpsLΔ4. Serial 10-fold dilutions starting at $10^5$ CFU/spot (from top to bottom) of the different mutants were spotted on plates with the indicated streptomycin concentrations. Chloramphenicol was supplemented at 35 μg/ml in all plates to maintain the plasmid. Plates were incubated overnight and photographed using MiniBis Pro (Bio-Imaging Systems). A representative experiment out of three is presented.

Figure 3:
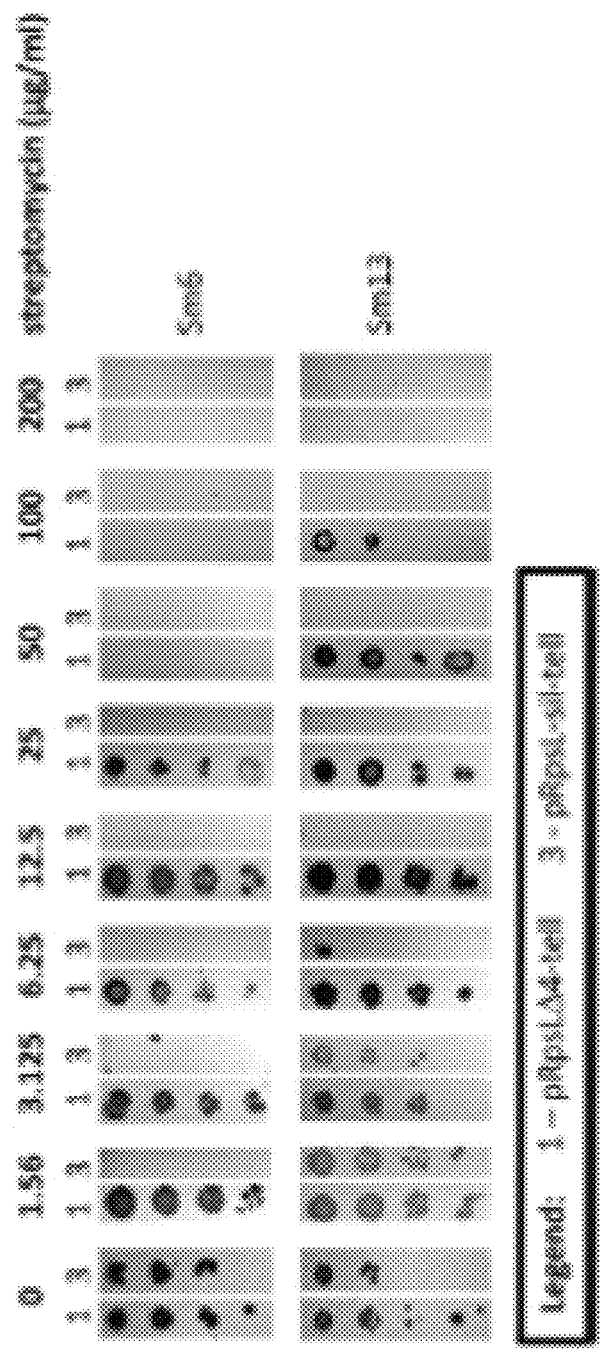

FIG. 3 is a photograph illustrating that tellurite-resistance genes efficiently replace chloramphenicol acetyl transferase as a selection marker. Streptomycin-resistant mutants transformed with a plasmid encoding wt rpsL as well as a tellurite-resistance gene, pRpsL-sil-tell, become more sensitive to streptomycin as compared to mutants transformed with a plasmid encoding a mock gene, pRpsLΔ4-tell. Serial 10-fold dilutions starting at $10^5$ CFU/spot (from top to bottom) of the different mutants were spotted on plates with the indicated streptomycin concentrations. Tellurite was supplemented at 1.5 μg/ml in all plates to maintain the plasmid. Plates were incubated overnight and photographed using MiniBis Pro (Bio-Imaging Systems). A representative experiment out of three is presented.

Figure 4:
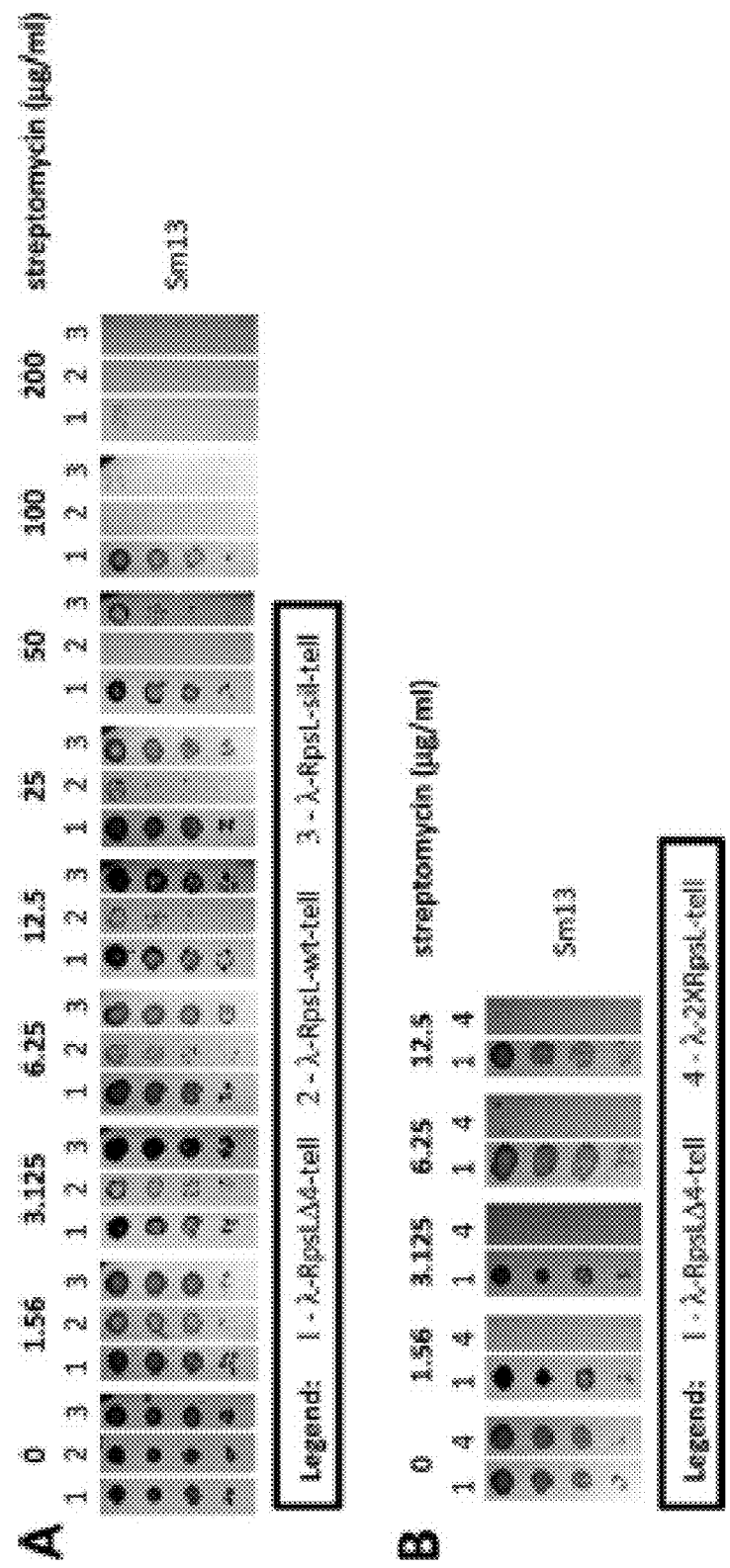

FIGS. 4A-B are photographs illustrating that rpsL genes introduced by phage λ sensitize a streptomycin-resistant mutant. Phage λ encoding a single copy of either wt rpsL (λ-RpsL-wt-tell) or rpsL-sil (λ-RpsL-sil-tell) sensitizes a streptomycin-resistant mutant, Sm13, compared to phage λ encoding a mock gene (λ-RpsLΔ4-tell) (A). Sensitization is significantly enhanced when the phage carries both copies of rpsL (λ-2xRpsL-tell) (B). Serial 10-fold dilutions starting at $10^5$ CFU/spot (from top to bottom) of the different lysogens were spotted on plates with the indicated streptomycin concentrations. Tellurite was supplemented at 1.5 μg/ml in all plates to maintain the prophage. Plates were incubated overnight and photographed using MiniBis Pro (Bio-Imaging Systems). A representative experiment out of three is presented.

Figure 5:

FIG. 5 is a photograph illustrating that gyrA introduced by phage λ sensitizes a nalidixic acid-resistant mutant. Phage λ encoding a single copy of wt gyrA (λ-GyrA-tell) sensitizes a nalidixic acid-resistant mutant, Nal2, compared to phage λ encoding a mock gene (λ-Ctrl-tell). Triplicates of the different lysogens, at $10^4$ CFU/spot, were spotted on plates with the indicated streptomycin concentrations. Tellurite was supplemented at 4 μg/ml in all plates. Plates were incubated overnight and photographed using MiniBis Pro (Bio-Imaging Systems). A representative experiment to out of three is presented.

Figure 6:
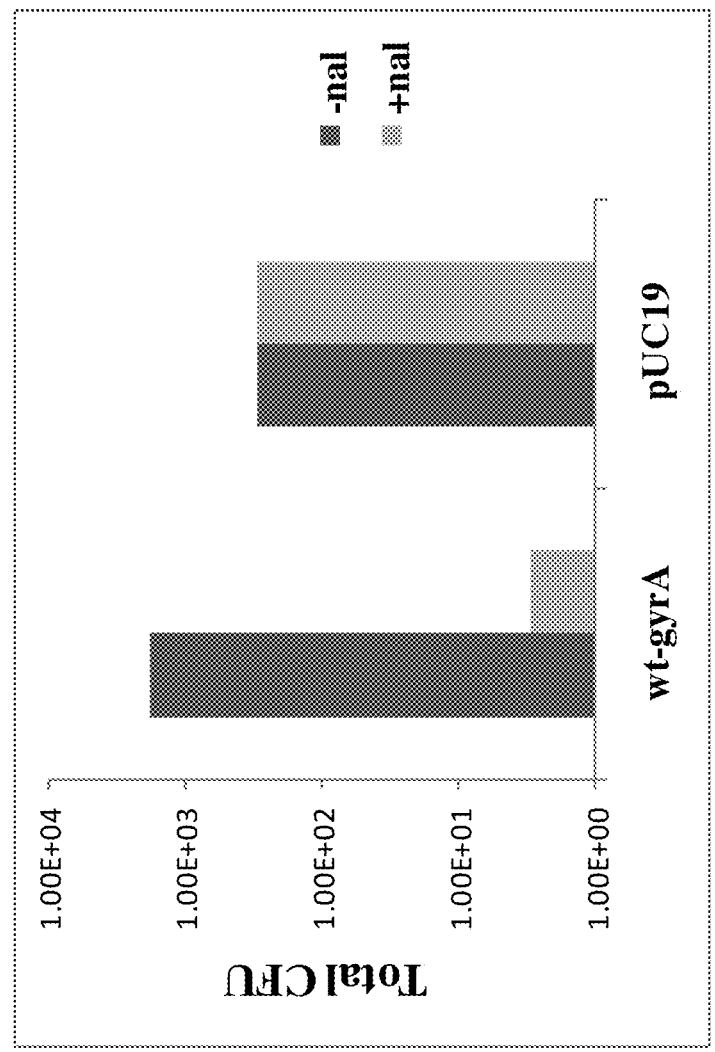

FIG. 6 is a bar graph illustrating that the gyrA gene restores sensitivity to nalidixic acid. An E. coli K-12 clone, having S83L substitution in its gyrA gene product conferring nalidixic acid (nal) resistance, was transformed with a pUC19 plasmid encoding the wt-gyrA or with pUC19 as control. Cells were grown to mid-log phase and serial dilutions were inoculated on plates containing 100 µg/ml amp+50 µg/ml nal (+nal) or 100 µg/ml amp only (−nal). Results show that the wt-gyrA gene renders the cells significantly more sensitive to killing by nal compared to the control.

Figure 7:
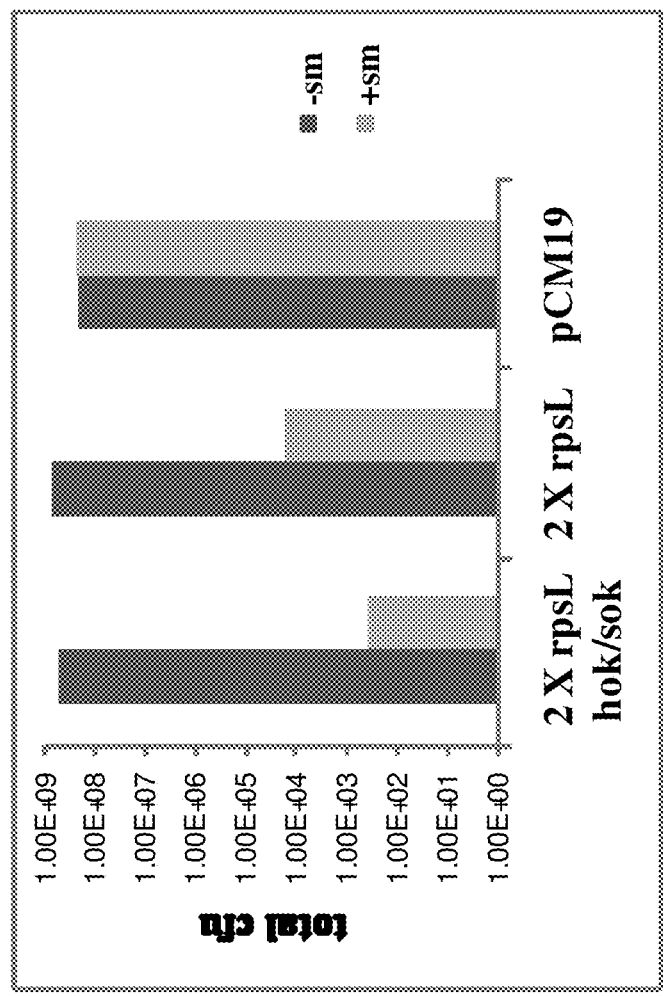

FIG. 7 is a bar graph illustrating the effectiveness of a toxin-antitoxin system for increasing sensitization to antibiotics by decreasing plasmid loss from the bacteria.

DESCRIPTION OF SPECIFIC EMBODIMENTS OF THE INVENTION

The present invention, in some embodiments thereof, relates to a method of reducing toxicity of bacteria and more particularly reducing antibiotic resistance in bacteria.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

According to the World Health Organization, bacteria resistant to antibiotics are one of the three main threats to human health. In the U.S. alone, there are almost 100,000 deaths each year due to infections. Hospitals are places especially critical in regard to the potential impact of bacterial resistance to antibiotics, which are home to people more vulnerable than normal to failing health, and also constitute a meeting point of various infectious bacteria, carried by the patients.

Most acquired bacterial resistance to streptomycin (an aminoglycoside antibiotic) is due to mutations in the rpsL (Ribosomal Protein Small subunit) gene. This gene encodes ribosomal protein S12. The present inventors isolated streptomycin resistant strains of E. coli K-12 by growth on streptomycin-containing agar plates (50 µg/ml). Resistant mutants arose at a rate of ~1 in $10^9$ CFUs. They isolated 22 mutant strains, 21 of which had mutations in rpsL. These specific mutations and their frequencies matched what had been previously observed in clinical isolates, thus were representative of the resistant strains encountered in clinical settings. Concentrating on two of these strains that carried the two point mutations most commonly observed in resistant isolates (one strain having the arginine-86→serine substitution, the other the lysine88→arginine change), the present inventors showed that transformation of resistant strains with plasmids carrying a wild-type (wt) rpsL gene rendered the transformants streptomycin sensitive, reducing the MICs of the two strains from 100 µg/ml to 12.5 µg/ml and from 200 µg/ml to 3.125 µg/ml, respectively (see FIGS. 2A-B).

The present inventors propose that the above findings may be adapted so as to enrich for antibiotic-treatable pathogens on hospital surfaces. This enriched, sensitive population might then interfere with the establishment of newly introduced resistant pathogens by overtaking their ecological niche.

Recombination events between the chromosomal resistant rpsL and the delivered wt rpsL may reduce the efficiency of the construct because it may eventually recombine with an rpsL copy that does not confer sensitivity on the transformed strains. Efficient homologous recombination requires a high degree of overall identity between two genes, as well as an identical "processing segment" of at least 23-27 bp. In E. coli, reducing overall identity from 100% to 90% decreases the frequency of recombination >40-fold. Accordingly, in order to minimize recombination between the introduced wt rpsL gene and the resident resistant rpsL gene, the present inventors modified the wt rpsL gene by introducing silent mutations at the third codon positions. This modified gene, called rpsL-sil (silent mutations), had only 62% identity to wt rpsL and none of the remaining regions of identity were long enough to serve as a minimum processing segment in recombination. Plasmids with the modified rpsL-sil gene were almost as efficient in restoring sensitivity.

Whilst further reducing the present invention to practice, the present inventors engineered λgt11 phage to encode both rpsL-sil and tellurite resistance (a gene which allows for resistance to the bacterial toxin, tellurite) and used them to infect one of their streptomycin resistant strains at 32° C. They selected lysogens on agar plates supplemented with tellurite. The streptomycin MIC for the lysogens was reduced from 200 µg/ml to 50 µg/ml (FIG. 4A). To further enhance sensitivity, the present inventors engineered a λgt11 phage that encoded two, one wt rpsL and one rpsL-sil. Lysogenization with this phage brought the streptomycin MIC down to 1.56 µg/ml (FIG. 4B), i.e., to the sensitivity observed in wt E. coli K-12, thus proving that engineered phages can efficiently and effectively restore streptomycin sensitivity to a resistant strain.

The present approach differs from conventional phage therapy in the sense that it does not use phages to kill the pathogens directly. Consequently, there is no selection against the used phage, but rather selection for pathogens harboring the phage because it contains tellurite resistance. Moreover, the approach avoids the use of phages inside the patient's body, thus overcoming toxicity issues and other drawbacks of phage therapy, such as phage neutralization by the spleen and the immune system.

Thus, according to one aspect of the present invention, there is provided a genetically modified bacteriophage comprising an exogenous polynucleotide which encodes an agent which reduces the toxicity of a bacterium.

As used herein, the term "bacteriophage" (also referred to herein as phage) refers to a virus of a bacterium. The bacteriophage may constitute a single or double-stranded DNA or RNA virus. The present inventors contemplate use of temperate, lytic or temperature-sensitive temperate bacteriophage, where at a particular temperature (e.g. at 36° C. or below) the phage favors lysogeny, whereas higher temperatures induce lytic production of the phage. An example of this type of phage is the λgt11 phage. Other λ phages having their cI gene changed to the cI857 allele are also contemplated since they will exhibit similar growth pattern. Preferably, the phage is selected such that it allows stable insertion of at least 1 kb of foreign DNA and more preferably at least 5 kb of foreign DNA.

According to another embodiment, the phage comprises deletion mutants with minimal genes and is capable of efficient lysogenization.

Other examples of phage contemplated by the present invention include those disclosed in U.S. Patent Application No. 20100322903, incorporated herein by reference.

Identification of phages capable of infecting additional bacteria is within the scope of one skilled in the art.

The phages used for infecting the bacteria may be capable of integrating into a gram positive or gram negative bacteria.

The term "Gram-positive bacteria" as used herein refers to bacteria characterized by having as part of their cell wall structure peptidoglycan as well as polysaccharides and/or teichoic acids and are characterized by their blue-violet color reaction in the Gram-staining procedure.

Representative Gram-positive bacteria include: *Actinomyces* spp., *Bacillus anthracis, Bifidobacterium* spp., *Clostridium botulinum, Clostridium perfringens, Clostridium* spp., *Clostridium tetani, Corynebacterium diphtheriae, Corynebacterium jeikeium, Enterococcus faecalis, Enterococcus faecium, Erysipelothrix rhusiopathiae, Eubacterium* spp., *Gardnerella vaginalis, Gemella morbillorum, Leuconostoc* spp., *Mycobacterium abcessus, Mycobacterium avium complex, Mycobacterium chelonae, Mycobacterium fortuitum, Mycobacterium haemophilium, Mycobacterium kansasii, Mycobacterium leprae, Mycobacterium marinum, Mycobacterium scrofulaceum, Mycobacterium smegmatis, Mycobacterium terrae, Mycobacterium tuberculosis, Mycobacterium ulcerans, Nocardia* spp., *Peptococcus niger, Peptostreptococcus* spp., *Proprionibacterium* spp., *Staphylococcus aureus, Staphylococcus auricularis, Staphylococcus capitis, Staphylococcus cohnii, Staphylococcus epidermidis, Staphylococcus haemolyticus, Staphylococcus hominis, Staphylococcus lugdanensis, Staphylococcus saccharolyticus, Staphylococcus saprophyticus, Staphylococcus schleiferi, Staphylococcus similans, Staphylococcus warneri, Staphylococcus xylosus, Streptococcus agalactiae* (group B *streptococcus*), *Streptococcus anginosus, Streptococcus bovis, Streptococcus canis, Streptococcus equi, Streptococcus milleri, Streptococcus mitior, Streptococcus mutans, Streptococcus pneumoniae, Streptococcus pyogenes* (group A *streptococcus*), *Streptococcus salivarius, Streptococcus sanguis*.

The term "Gram-negative bacteria" as used herein refer to bacteria characterized by the presence of a double membrane surrounding each bacterial cell. Representative Gram-negative bacteria include *Acinetobacter calcoaceticus, Actinobacillus actinomycetemcomitans, Aeromonas hydrophila, Alcaligenes xylosoxidans, Bacteroides, Bacteroides fragilis, Bartonella bacilliformis, Bordetella* spp., *Borrelia burgdorferi, Branhamella catarrhalis, Brucella* spp., *Campylobacter* spp., *Chalmydia pneumoniae, Chlamydia psittaci, Chlamydia trachomatis, Chromobacterium violaceum, Citrobacter* spp., *Eikenella corrodens, Enterobacter aerogenes, Escherichia coli, Flavobacterium meningosepticum, Fusobacterium* spp., to *Haemophilus influenzae, Haemophilus* spp., *Helicobacter pylori, Klebsiella* spp., *Legionella* spp., *Leptospira* spp., *Moraxella catarrhalis, Morganella morganii, Mycoplasma pneumoniae, Neisseria gonorrhoeae, Neisseria meningitidis, Pasteurella multocida, Plesiomonas shigelloides, Prevotella* spp., *Proteus* spp., *Providencia rettgeri, Pseudomonas aeruginosa, Pseudomonas* spp., *Rickettsia prowazekii, Rickettsia rickettsii, Rochalimaea* spp., *Salmonella* spp., *Salmonella typhi, Serratia marcescens, Shigella* spp., *Treponema carateum, Treponema pallidum, Treponema pallidum endemicum, Treponema pertenue, Veillonella* spp., *Vibrio cholerae, Vibrio vulnificus, Yersinia enterocolitica, Yersinia pestis*.

Specific examples of *E. coli* include, but are not limited to enteroaggregative (EAEC), enterohemorrhagic (EHEC), enteroinvasive (EIEC), enteropathogenic (EPEC), enterotoxigenic (ETEC) and diffuse adherent (DAEC) *E. coli*.

An exemplary *E. coli* serotype contemplated by the present invention is O157:H7.

Modification of the bacteriophage of this aspect of embodiments of the present invention may be effected using any method known in the art, including standard cloning techniques, artificial selection for host-range mutants, and homologous recombination.

Agents which reduce the toxicity of a bacteria include agents which reduce the ability of the bacteria to bring about infection in mammalian cells. The agents may be capable of reducing the virulence of a bacteria or may be capable of reversing resistance to an antibiotic agent. According to this embodiment, the agent does not directly affect the survival of the bacteria.

Agents which may be expressed in the bacteriophage include both polypeptide and polynucleotide agents (an siRNA, a short hairpin RNA, a ribozyme and a DNAzyme). Such agents are further described herein below.

In order to express an exogenous polypeptide or polynucleotide agent in a bacteriophage, a polynucleotide encoding the polypeptide (or the polynucleotide agent) is inserted into the phage DNA under control of a promoter which is active in the bacteria.

Examples of phage promoters which may be used in the context of the present invention are disclosed in U.S. Patent Application No. 20100322903, incorporated herein by reference.

According to one embodiment, the bacteriophages are used to reverse the antibiotic resistance bacteria expressing an antibiotic resistant gene that is a dominant sensitive antibiotic resistant gene.

Such genes include the rpsl gene (Genebank NC_000913 nt 3472200-3472574—SEQ ID NO: 23) encoding the 30S ribosomal subunit protein S12, mutations of which are known to cause resistance to streptomycin; the gyrA gene encoding the gyrase protein (Genebank NC_000913 nt 2334815.2337442—SEQ ID NO: 26), mutations of which are known to cause resistance to quinolone antibiotics such as nalidixic acid, the rpoB gene (SEQ ID NO: 28) that encodes the RNA Polymerase β Subunit, mutations of which are known to cause resistance to rifamycin and the thyA gene (Genebank NC_000913 nt 2962383-2963177—SEQ ID NO: 30) that encodes thymidylate synthase, mutations of which are known to cause resistance to trimethoprim.

The amino acid sequence of the wild-type 30S ribosomal subunit protein S12 is set forth in SEQ ID NO: 25.

The amino acid sequence of the wild-type gyrase protein is set forth in SEQ ID NO: 27.

The amino acid sequence of the wild-type RNA Polymerase β Subunit is set forth in SEQ ID NO: 29.

The amino acid sequence of the wild-type thymidylate synthase is set forth in SEQ ID NO: 31.

Accordingly, the present inventors contemplate modifying bacteriophage by inserting polynucleotide sequences encoding SEQ ID NO: 25, 27, 29 and/or 31 therein.

The present invention further contemplates modifying the polynucleotide sequences in order to minimize recombination between the introduced wildtype genes and the resident resistant gene which would reduce the effectiveness of the strategy. Efficient homologous recombination requires a high degree of overall identity between the two genes, as well as an identical "processing segment" of at least 23-27 bp. In *E. coli*, reducing overall identity from 100% to 90% decreases the frequency of recombination >40-fold. Thus, the present invention contemplates modifying the wt rpsL gene by introducing silent mutations (e.g. at the third codon positions) so as not to affect the amino acid sequence of the encoded proteins.

The modified genes may be about 90% identical, 80% identical, 70% identical, 60% identical or even 50% identical to the wildtype genes. Preferably, none of the remaining regions of identity are long enough to serve as a minimum processing segment in recombination.

An exemplary polynucleotide sequence encoding wild-type 30S ribosomal subunit protein S12, modified so as to prevent homologous recombination is set forth in SEQ ID NO: 24.

It will be appreciated that the bacteriophages of this aspect of the present invention may also be modified to express more than one of the above disclosed dominant-sensitive genes. Additionally, or alternatively, the bacteriophages of this aspect of the present invention may be modified to express more than one copy of any one of the above mentioned wild-type dominant-sensitive genes.

As mentioned, additionally, or alternatively, the bacteriophages of this aspect of the present invention may be genetically modified to express polynucleotide agents (RNA silencing agents) capable of downregulating expression of genes responsible for antibiotic resistance or bacterial virulence.

The phrase "antibiotic resistance genes" as used herein refers to genes that confer resistance to antibiotics, for example by coding for enzymes which destroy it, by coding for surface proteins which prevent it from entering the microorganism, actively exports it, or by being a mutant form of the antibiotic's target so that it can ignore it.

Example of antibiotic resistance genes may be found on the ARDB—Antibiotic Resistance Genes Database. Particular examples of antibiotic resistance genes include, but are not limited to extended-spectrum beta lactamse (ESBL) genes, methicillin resistance gene, CTX-M-15; ndm-1,2,5,6 or a vancomycin resistance gene.

As mentioned, as well as targeting antibiotic resistance genes, the siRNAs of this aspect of the present invention may be targeted against virulence genes. Preferably, the RNA silencing agents of this aspect of the present invention do not target a gene that affects the propagation and/or respiration of the bacteria (i.e. essential genes).

The phrase "virulence gene" as used herein refers to a nucleic acid sequence of a microorganism, the presence and/or expression of which correlates with the pathogenicity of the microorganism. In the case of bacteria, such virulence genes may in an embodiment comprise chromosomal genes (i.e. derived from a bacterial chromosome), or in a further embodiment comprise a non-chromosomal gene (i.e. derived from a bacterial non-chromosomal nucleic acid source, such as a plasmid). In the case of E. coli, examples of virulence genes and classes of polypeptides encoded by such genes are described below. Virulence genes for a variety of pathogenic microorganisms are known in the art.

Examples of virulence genes include, but are not limited to genes encoding toxins (e.g. Shiga toxin and cholera toxin), hemolysins, fimbrial and afimbrial adhesins, cytotoxic factors, microcins and colicins and also those identified in Sun et al., Nature Medicine, 2000; 6 (11): 1269-1273.

According to one embodiment of the invention, the bacterial virulence gene may be selected from the group consisting of actA (example is given in genebank accession no: NC_003210.1), Tem (example is given in genebank accession no: NC_009980), Shy (example is given in genebank accession no: NC_009648), oxa-1 (example is given in genebank accession no: NW_139440), oxa-7 (example is given in genebank accession no: X75562), pse-4 (example is given in genebank accession no: J05162), ctx-m (example is given in genebank accession no: NC_010870), ant(3")-Ia (aadA1) (example is given in genebank accession no: DQ489717), ant(2")-Ia (aadB)b (example is given in genebank accession no: DQ176450), aac(3)-IIa (aacC2) (example is given in genebank accession no: NC_010886), aac(3)-IV (example is given in genebank accession no: DQ241380), aph(3')-Ia (aphA1) (example is given in genebank accession no: NC_007682), aph(3')-IIa (aphA2) (example is given in genebank accession no: NC_010170), tet(A) (example is given in genebank accession no: NC_005327), tet(B) (example is given in genebank accession no: FJ411076), tet(C) (example is given in genebank accession no: NC_010558), tet(D) (example is given in genebank accession no: NC_010558), tet(E) (example is given in genebank accession no: M34933), tet(Y) (example is given in genebank accession no: AB089608), catI (example is given in genebank accession no: NC_005773), catII NC_010119, catIII (example is given in genebank accession no: X07848), floR (example is given in genebank accession no: NC_009140), dhfrI (example is given in genebank accession no: NC_002525), dhfrV (example is given in genebank accession no: NC_010488), dhfrVII (example is given in genebank accession no: DQ388126), dhfrIX (example is given in genebank accession no: NC_010410), dhfrXIII (example is given in genebank accession no: NC_000962), dhfrXV (example is given in genebank accession no: Z83311), suII (example is given in genebank accession no: NC_000913), suIII (example is given in genebank accession no: NC_000913), integron class 1 3'-CS (example is given in genebank accession no: AJ867812), vat (example is given in genebank accession no: NC_011742), vatC (example is given in genebank accession no: AF015628), vatD (example is given in genebank accession no: AF368302), vatE (example is given in genebank accession no: NC_004566), vga (example is given in genebank accession no: AF117259), vgb (example is given in genebank accession no: AF117258), and vgbB (example is given in genebank accession no: AF015628).

As used herein, the phrase "RNA silencing" refers to a group of regulatory mechanisms [e.g. RNA interference (RNAi), transcriptional gene silencing (TGS), post-transcriptional gene silencing (PTGS), quelling, co-suppression, and translational repression] mediated by RNA molecules which result in the inhibition or "silencing" of the expression of a corresponding protein-coding gene. RNA silencing has been observed in many types of organisms, including plants, animals, and fungi.

As used herein, the term "RNA silencing agent" refers to an RNA which is capable of specifically inhibiting or "silencing" the expression of a target gene. In certain embodiments, the RNA silencing agent is capable of preventing complete processing (e.g, the full translation and/or expression) of an mRNA molecule through a post-transcriptional silencing mechanism. RNA silencing agents include noncoding RNA molecules, for example RNA duplexes comprising paired strands, as well as precursor RNAs from which such small non-coding RNAs can be generated. Exemplary RNA silencing agents include dsRNAs such as siRNAs, miRNAs and shRNAs. In one embodiment, the RNA silencing agent is capable of inducing RNA interference. In another embodiment, the RNA silencing agent is capable of mediating translational repression.

According to an embodiment of the invention, the RNA silencing agent is specific to the target RNA and does not cross inhibit or silence a gene or a splice variant which exhibits 99% or less global homology to the target gene, e.g., less than 98%, 97%, 96%, 95%, 94%, 93%, 92%, 91%, 90%, 89%, 88%, 87%, 86%, 85%, 84%, 83%, 82%, 81% global homology to the target gene.

RNA interference refers to the process of sequence-specific post-transcriptional gene silencing in animals mediated by short interfering RNAs (siRNAs). The corresponding process in plants is commonly referred to as post-transcriptional gene silencing or RNA silencing and is also referred to as quelling in fungi. The process of post-transcriptional gene silencing is thought to be an evolutionarily-conserved cellular defense mechanism used to prevent the expression of foreign genes and is commonly shared by diverse flora and phyla. Such protection from foreign gene expression may have evolved in response to the production of double-stranded RNAs (dsRNAs) derived from viral infection or from the random integration of transposon elements into a host genome via a cellular response that specifically destroys homologous single-stranded RNA or viral genomic RNA.

Accordingly, some embodiments of the invention contemplates use of dsRNA to downregulate protein expression from mRNA.

According to one embodiment, the dsRNA is greater than 30 bp. (siRNAs).

According to another embodiment, the dsRNA is an siRNA.

The term "siRNA" refers to small inhibitory RNA duplexes (generally between 18-30 basepairs) that induce the RNA interference (RNAi) pathway.

The strands of a double-stranded interfering RNA (e.g., an siRNA) may be connected to form a hairpin or stem-loop structure (e.g., an shRNA). Thus, as mentioned the RNA silencing agent of some embodiments of the invention may also be a short hairpin RNA (shRNA).

The term "shRNA", as used herein, refers to an RNA agent having a stem-loop structure, comprising a first and second region of complementary sequence, the degree of complementarity and orientation of the regions being sufficient such that base pairing occurs between the regions, the first and second regions being joined by a loop region, the loop resulting from a lack of base pairing between nucleotides (or nucleotide analogs) within the loop region. The number of nucleotides in the loop is a number between and including 3 to 23, or 5 to 15, or 7 to 13, or 4 to 9, or 9 to 11. Some of the nucleotides in the loop can be involved in base-pair interactions with other nucleotides in the loop. Examples of oligonucleotide sequences that can be used to form the loop include 5'-UUCAAGAGA-3' (Brummelkamp, T. R. et al. (2002) Science 296: 550) and 5'-UUUGUGUAG-3' (Castanotto, D. et al. (2002) RNA 8:1454). It will be recognized by one of skill in the art that the resulting single chain oligonucleotide forms a stem-loop or hairpin structure comprising a double-stranded region capable of interacting with the RNAi machinery.

Methods of designing siRNA agents for downregulating gene expression in bacteria are provided in Nakashima et al Nucleic Acids Research, 2006, Vol. 34, No. 20 and Cheng et al., Nucleic Acids Research, 2009, 1-15, the contents of which are incorporated herein by reference.

Another agent capable of downregulating expression in bacteria is a DNAzyme molecule capable of specifically cleaving an mRNA transcript or DNA sequence of the mutated antibiotic resistance gene. DNAzymes are single-stranded polynucleotides which are capable of cleaving both single and double stranded target sequences (Breaker, R. R. and Joyce, G. Chemistry and Biology 1995; 2:655; Santoro, S. W. & Joyce, G. F. Proc. Natl, Acad. Sci. USA 1997; 943: 4262) A general model (the "10-23" model) for the DNAzyme has been proposed. "10-23" DNAzymes have a catalytic domain of 15 deoxyribonucleotides, flanked by two substrate-recognition domains of seven to nine deoxyribonucleotides each. This type of DNAzyme can effectively cleave its substrate RNA at purine:pyrimidine junctions (Santoro, S. W. & Joyce, G. F. Proc. Natl, Acad. Sci. USA 199; for rev of DNAzymes see Khachigian, L M [Curr Opin Mol Ther 4:119-21 (2002)].

Another agent capable of downregulating expression in bacteria is a ribozyme molecule capable of specifically cleaving its mRNA transcript. Ribozymes are being increasingly used for the sequence-specific inhibition of gene expression by the cleavage of mRNAs encoding proteins of interest [Welch et al., Curr Opin Biotechnol. 9:486-96 (1998)]. The possibility of designing ribozymes to cleave any specific target RNA has rendered them valuable tools in both basic research and therapeutic applications. In the therapeutics area, ribozymes have been exploited to target viral RNAs in infectious diseases, dominant oncogenes in cancers and specific somatic mutations in genetic disorders [Welch et al., Clin Diagn Virol. 10:163-71 (1998)]. Most notably, several ribozyme gene therapy protocols for HIV patients are already in Phase 1 trials. More recently, ribozymes have been used for transgenic animal research, gene target validation and pathway elucidation. Several ribozymes are in various stages of clinical trials. ANGIOZYME was the first chemically synthesized ribozyme to be studied in human clinical trials. ANGIOZYME specifically inhibits formation of the VEGF-r (Vascular Endothelial Growth Factor receptor), a key component in the angiogenesis pathway. Ribozyme Pharmaceuticals, Inc., as well as other firms have demonstrated the importance of anti-angiogenesis therapeutics in animal models. HEPTAZYME, a ribozyme designed to selectively destroy Hepatitis C Virus (HCV) RNA, was found effective in decreasing Hepatitis C viral RNA in cell culture assays (Ribozyme Pharmaceuticals, Incorporated—WEB home page).

Preferably, the polynucleotides used to modify the bacteriophages of this aspect of the present invention encode a selectable marker so that positive transformants may be selected.

As used herein, the phrase "a selectable marker" refers to a trait that protects the organism from a selective agent that would normally kill it or prevent its growth.

Marker genes include genes encoding antibiotic resistance, such as those encoding neomycin phosphotransferase II (NEO) and hygromycin phosphotransferase (HPT), as well as genes conferring resistance to herbicidal compounds, such as glufosinate ammonium, bromoxynil, imidazolinones, and 2,4-dichlorophenoxyacetate (2,4-D). The above list of selectable marker genes is not meant to be limiting. Any selectable marker gene can be used in the present invention.

According to a particular embodiment, the selectable marker is one that confers resistance to a toxic (bactericidal) compound.

For the purposes of this invention, an agent may be considered to be an antibiotic if it is at least 5 fold (and more preferably 10) fold more lethal to bacteria than to mammalian cells whereas a toxic compound has is less than 10 fold and more preferably less than 5 fold more lethal to bacteria that to mammalian cells.

According to another embodiment, the selectable marker is not an antibiotic resistance gene.

According to a specific embodiment, the polynucleotide encodes the tehAB operon (SEQ ID NO: 32) which confers resistance against potassium-tellurite ($K_2TeO_3$). Tellurite is a toxic compound to bacteria as it forms long lived sulfur complexes, thus disrupting the thiol balance within the cells. The tehAB genes increase the minimal inhibitory concentration (MIC) of tellurite against E. coli 50-100 fold upon expression from an active promoter, although they do not confer resistance to the E. coli when present in the chromosome under their endogenous promoter. The observed MIC of E. coli either having or lacking the chromosomal tehAB genes is 2 µg/ml compared to a MIC of 128 µg/ml in cells harboring an extrachromosomal tehAB with an active promoter.

Additional toxins that may be used as selectable markers include chlorhexidine salts, diamidines, acridines, arsenite, arsenate and antimonite.

Additional methods to counteract antibiotic pressure and to maintain the stability of the plasmid conferring sensitivity to antibiotics include use of a toxin-antitoxin system. In such systems, a long lived toxin and a short lived antitoxin are encoded. The antitoxin, which is constantly produced, eliminates the toxin activity as long as the encoding DNA is present in the cell. However, if the DNA is lost, the long lived toxin exerts its effect resulting in cell death as no antitoxin is encoded to counteract it. Genetic linkage of such a system to the DNA sensitizing cassette should maintain the DNA construct despite antibiotic treatment. Pathogens that lose the DNA construct are killed by the toxin because they lose the antitoxin encoding DNA. As illustrated in FIG. 7, sensitization to antibiotics increased more than 100 fold upon linking one such system, the hok/sok, to streptomycin-sensitizing genes.

Other toxin antitoxin systems that may be used in accordance with the present invention include phd/doc; mazE/mazF; RNAII; T is/B; LdrD/RdlD; FlmA/FlmB; Ibs/Sib; TxpA/RatA; SymE/SymR; XCV2162/ptaRNA1; CcdB/CcdA; ParE/ParD; yafO/yafN; HicB/HicA; Kid/Kis.

To further overcome possible loss of the drug-sensitizing genes the toxin antitoxin system may be designed such that their presence will be required for acquisition of tellurite resistance, and therefore their expression will be advantageous to the pathogens.

For example, the sensitizing genes may be positioned before the promoter-less tellurite-resistance genes. Tellurite resistance will be thus dependent on expression of the sensitizing genes. In addition, the DNA construct transferred with tellurite resistance may be flanked by genetic markers whose role is to ensure that tellurite resistance is conferred only when the complete drug-sensitizing cassette is present in the bacterium. Such markers may encode the short ~100 bp amber and ochre suppressor tRNA genes. In this case, the tellurite resistance genes typically should harbor both amber and ochre stop codons. The amber and ochre tRNA genes will act as suppressors, allowing translation of the tellurite resistance gene despite the presence of the stop codons. In the event that only a portion of the cassette is transferred, the tellurite resistance will not be expressed due to absence of one or two of the tRNA suppressors and/or the promoter.

The present inventors contemplate use of the above described bacteriophages to infect bacterial populations on solid surfaces, rendering antibiotic insensitive bacteria residing thereon to become sensitive to antibiotic.

Cocktails of different bacteriophages may be applied to solid surface, each bacteriophage having a different host specificity, each carrying genes for tellurite (or other similar toxic compound) resistance as well as genes that confer dominant sensitivity to a variety of antibiotics. It will be appreciated that the bacteriophages are not bactericidal to their hosts since the bacteriophages are not modified to express agents that are toxic to bacteria. Accordingly, in order to enrich for antibiotic-sensitive populations, the present invention further contemplates contacting the solid surface with the bactericidal protein product of the selectable marker encoded in the phage. Thus, for example, in the case where the genetically modified bacteriophage encodes the tehAB operon, the solid surface is also contacted with tellurite.

The enriched, antibiotic-sensitive populations might then interfere with the establishment of newly introduced resistant pathogens by overtaking their ecological niche. The present approach differs from conventional phage therapy in the sense that it does not use phages to kill the pathogens directly. Consequently, there is no selection against the used phage, but rather selection for pathogens harboring the phage because it contains tellurite resistance. Moreover, the approach avoids the use of phages inside the patient's body, thus overcoming toxicity issues and other drawbacks of phage therapy, such as phage neutralization by the spleen and the immune system.

As used herein the term "contacting" refers to the positioning of the bacteriophages (and optionally, the toxic compound) of the present invention such that they are in direct or indirect contact with the bacterial cells. Thus, the present invention contemplates both applying the bacteriophages (and optionally the toxic compound) of the present invention to a desirable surface and/or directly to the bacterial cells.

Contacting surfaces with the bacteriophages (and optionally the toxic compound) can be effected using any method known in the art including spraying, spreading, wetting, immersing, dipping, painting, ultrasonic welding, welding, bonding or adhering.

The present invention envisages contacting a wide variety of surfaces with the bacteriophages (and optionally, the toxic compound) of the present invention including fabrics, fibers, foams, films, concretes, masonries, glass, metals, plastics, polymers, and like.

According to a particular embodiment, the bacteriophages (and optionally, the toxic compound) are contacted with surfaces present in a hospital, hospice, old age home, or other such care facility.

Other surfaces related to health include the inner and outer aspects of those articles involved in water purification, water storage and water delivery, and those articles involved in food processing. Thus the present invention envisions coating a solid surface in a food or beverage factory.

Surfaces related to health can also include the inner and outer aspects of those household articles involved in providing for nutrition, sanitation or disease prevention. Thus, the bacteriophages (and optionally toxic compound) of the present invention may also be used for disinfecting toilet bowls etc.

According to one embodiment, the bacteriophages and toxic compound are applied every 12 hours, daily, 6 times a week, 5 times a week, four times a week, three times a week, twice a week or even once a week to the solid surface.

The bacteriophages and toxic compound may be applied concurrently, or one following the other. Alternatively, the bacteriophages may be applied on consecutive days.

Once novel genetically modified bacteriophages are generated they may be tested against specific pathogens such as *M. tuberculosis* and Extended Spectrum Beta Lactamase (ESBL) *Klebsiella pneumoniae*. For safety reasons, lack of toxins in each new lysogenizing phage should be tested. Mice cages may be used to simulate hospital rooms, and mice to simulate patients. In one exemplary test, all cages may be spread with resistant pathogens. The efficiency of the engineered phages to enrich for to drug-sensitive pathogen population in cages may be assessed by spraying phages followed by tellurite for several days. Mice may then be put in these cages or untreated cages, and those developing bacterial disease will be treated with antibiotics. It is expected that mice in the phage-treated cages will be cured by the antibiotics whereas mice in the control cages will succumb to the bacterial disease.

It is expected that during the life of a patent maturing from this application many relevant selectable markers and corresponding toxic compounds will be developed and the scope of those terms are intended to include all such new technologies a priori.

As used herein the term "about" refers to ±10%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases to "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et to al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Culture of Animal Cells—A Manual of Basic Technique" by Freshney, Wiley-Liss, N.Y. (1994), Third Edition; "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

Materials and Methods

Bacterial Strains.

A partial list of bacterial strains used in this study are listed to in Table 1.

TABLE 1

| Source | Description | E. coli strain |
|---|---|---|
| Lab collection | Wild type | K-12 |
| Stratagene | e14-(McrA-) Δ(lac)U169 supE supF hsdR metB trpR tonA21 proC::Tn5 (Kan^r) [pMC9 Amp^r Tet^r] | Y1088 |
| Lab collection | supF58, supE44, mel-1, F^+ | Ymel |

Table 2 recites the *E. coli* K-12 streptomycin-resistant mutants, Sm1-22, isolated on 50 µg/ml streptomycin. Substitutions in the RpsL protein are indicated, as well as the MIC to streptomycin.

TABLE 2

| MIC (mg/ml) | Substitution in RpsL | Streptomycin-resistant mutant |
|---|---|---|
| ≥50 | P42S | Sm1 |
| 800 | K43L | Sm2 |
| ≥50 | K43N | Sm3 |
| ≥50 | R54S | Sm4 |
| ≥50 | R86S | Sm5 |
| 100 | R86S | Sm6 |
| ≥50 | R86S | Sm7 |
| ≥50 | R86S | Sm8 |
| ≥50 | R86S | Sm9 |
| ≥50 | R86S | Sm10 |
| ≥50 | K88E | Sm11 |
| 400 | K88R | Sm12 |
| 400 | K88R | Sm13 |
| 400 | K88R | Sm14 |
| 400 | K88R | Sm15 |
| 400 | K88R | Sm16 |
| 400 | K88R | Sm17 |
| 400 | K88R | Sm18 |
| 400 | K88R | Sm19 |
| 400 | K88R | Sm20 |
| 400 | K88R | Sm21 |
| ≥50 | none | Sm22 |

Table 3 recites *E. coli* K-12 nalidixic acid-resistant mutants, Nal1-8, isolated on 50 µg/ml nalidixic acid. Substitutions in the GyrA protein are indicated, as well as the MIC to nalidixic acid.

TABLE 3

| MIC (µg/ml) | Substitution in GyrA | Nalidixic acid-resistant mutant |
|---|---|---|
| ≥50 | S83L | Nal1 |
| ≥50 | S83L | Nal2 |
| ≥50 | S83L | Nal3 |
| 128 | D87G | Nal4 |
| 128 | D87G | Nal5 |
| 128 | D87G | Nal6 |
| 128 | D87G | Nal7 |
| 128 | D87G | Nal8 |

Oligonucleotides used in this study are listed in 4.

TABLE 4

| Sequence | Primer |
|---|---|
| CAATAACCCTGATAAATGCTTCAATAATATTGAAA AAGGAAGAGTACTAGTATGCAGAGCGATAAAGTGC TCAA<br>SEQ ID NO: 1 | N1 |
| AAGTTTTAAATCAATCTAAAGTATATATGAGTAAA CTTGGTCTGACAGCTCGAGTCATTTTTTACGTGCC AGCA<br>SEQ ID NO: 2 | N2 |
| TCGTTTTACAACGTCGTGGATCCTTACCAATGCTT AATCAGTGAGGCTCGGATTATCAAAAAGGATCTTC ACCTAGATCC<br>SEQ ID NO: 3 | RE22 |
| ACTTAAGCTTAAAAGAGTATTGACTTAAAGTCAA CTATAGGATACTTACAGCCATAGGAGGACAGCTAT GGCAACAGTTAACCAGCT<br>SEQ ID NO: 4 | 217Fa |
| TTCGGAATTCTTAAGCCTTAGGACGCTTCA<br>SEQ ID NO: 5 | 217R |
| GCTAGAATTCGGCGACGGCTTCAAATTTAG<br>SEQ ID NO: 6 | 220Fa |
| CATATGTTATTC TTCTTCTGGC TCGTC<br>SEQ ID NO: 7 | 220Ra |
| ACTTTCTAGAAGGAAACAGCTATGACCATG<br>SEQ ID NO: 8 | 223R |
| TAACGGATCCTTACCAATGCTTAATCAGTG<br>SEQ ID NO: 9 | 223F |
| TAACGGATCCACGACGTTGTAAAACGACGG<br>SEQ ID NO: 10 | 224F |
| ACTTTCTAGAAGGTGAAGATCCTTTTTGAT<br>SEQ ID NO: 11 | 224R |
| ACGCCAATTGGTATGTTGTGTGGAATTGTG<br>SEQ ID NO: 12 | 231R |
| CGTTCAATTGGTTAAGGGATTTTGGTCATG<br>SEQ ID NO: 13 | 231F |
| CAGACATGTATACCCCGTAC<br>SEQ ID NO: 14 | 232F |
| TACGCCATGGCCGGAGTGGC<br>SEQ ID NO: 15 | 232R |
| GTGTGAAATTGTTATCCGCT<br>SEQ ID NO: 16 | 233F |
| ACTGACTAGTACTCTTCCTTTTTCAATATTATTG<br>SEQ ID NO: 17 | 234Fb |
| CTGTCAGACCAAGTTTACTCCTGTCAGACCAAGTT TACTC<br>SEQ ID NO: 18 | 234R |
| ACTGACTAGTATGGAGAAAAAAATCACTGG<br>SEQ ID NO: 19 | 235Fb |
| TTCACTCGAGTTACGCCCCGCCCTGCCACTC<br>SEQ ID NO: 20 | 235R |

Isolation of Resistant Mutants.

Over twenty different overnight cultures of a total of ~$10^{11}$ *E. coli* K-12 cells were inoculated on Luria-Bertani (LB)-agar plates containing 50 µg/ml streptomycin or 50 µg/ml nalidixic acid. Resistant mutants emerged, in both cases, at a median frequency of ~1 in $10^9$ CFU, and were picked from different cultures, to reduce the occurrence of sibling mutants. These bacteria were streaked on an agar plate containing the appropriate antibiotic. The rpsL or gyrA genes of resistant mutants emerging on the plate were PCR-amplified followed by DNA sequencing.

Plasmid Construction.

Plasmids were constructed using standard molecular to biology techniques. DNA segments were amplified by PCR. Standard digestion of the PCR products and vector by restriction enzymes was carried out according to the manufacturer's instructions.

rpsL-wt, rpsL-sil, and gyrA Cloning.

The rpsL gene with multiple silent mutations was designed and supplied by IDT. An EcoRI-HindIII fragment containing a mutated A1 T7 promoter, consensus Shine-Dalgarno (SD) and the rpsL-sil open reading frame (ORF) was cloned into a pUC19 plasmid (HindIII-EcoRI). Wild type rpsL was amplified from the E. coli chromosome using primers 217Fa/217R containing the same mutated A1 T7 promoter and SD, and cloned into a pUC19 plasmid (HindIII-EcoRI). For construction of p2XRpsL-tell, the rpsL-wt and rpsL-Sil were first cloned on the same plasmid. These genes were amplified with primers 223F/R and 224F/R, respectively, and cloned in pUC19. Primers 220Fa/Ra were used for amplification of the gyrA gene containing its endogenous promoter and its known transcription repression and activation sites. The resulting PCR product was cloned as an EcoRI-NdeI fragment.

Replacement of the Ampicillin Resistance Gene and Construction of RpsL Mock Gene.

In order to replace the antibiotic marker of pUC19, encoding the bla gene, the cat gene was amplified from plasmid pACYC184 using primers 235Fb/R and digested with SpeI-XhoI. The pUC plasmids described above were PCR amplified using primers 234Fb/234R, digested with SpeI-XhoI and ligated to the cm fragment, resulting in plasmids pRpsl-wt, pRpsl-sil, p2xRpsL and pGyrA. To construct plasmid pRpsLΔ4, pRpsL-wt was digested with SphI, blunt ended using Quick Blunting Kit (NEB) and religated. This procedure deleted 4 base pairs (bp) resulting in a frame shift after amino acid 26 of the RpsL protein.

Phages.

Figure 1A:
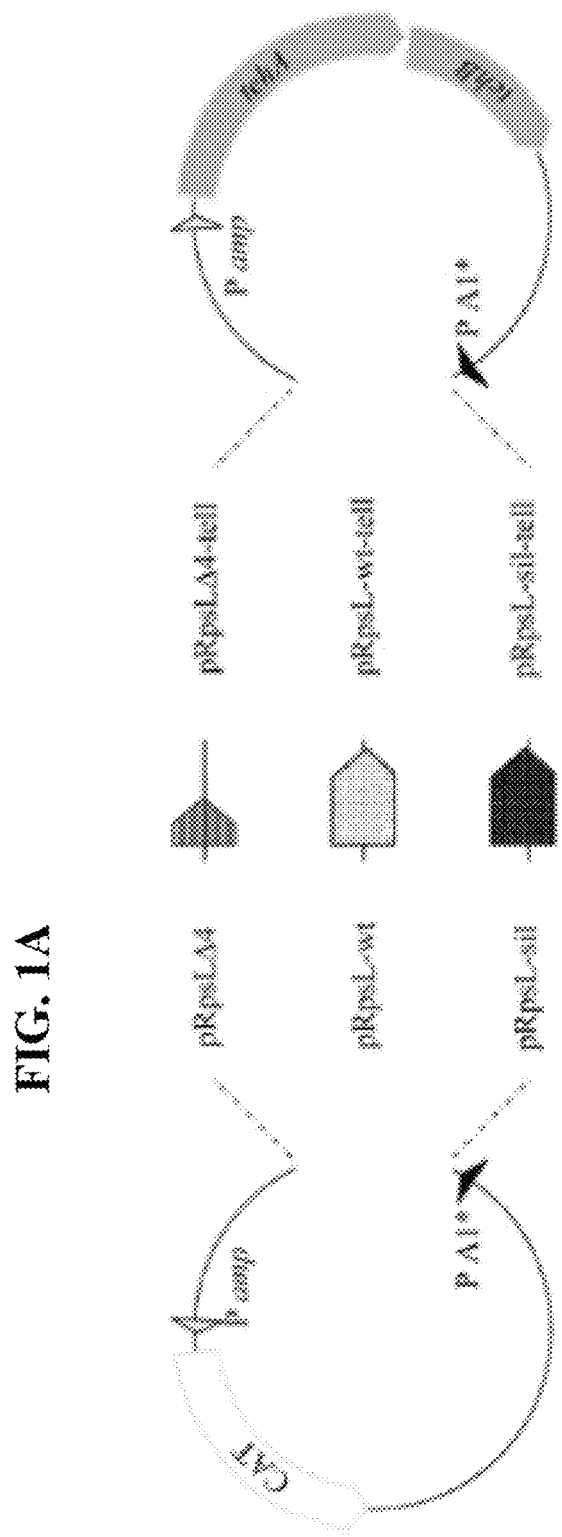
FIGS. 1A-B are maps of plasmid (A) and phage (B). The inserts are drawn to scale, with the relevant genes and genetic elements indicated. CAT—chloramphenicol acetyl transferase, conferring chloramphenicol resistance; Pamp—bla promoter, P A1*—mutated T7-A1 promoter of T7 phage. The promoter could not be cloned without a mutation, and therefore the following 1 bp deletion in the promoter sequence (bolded) was inserted.
Figure 1B:
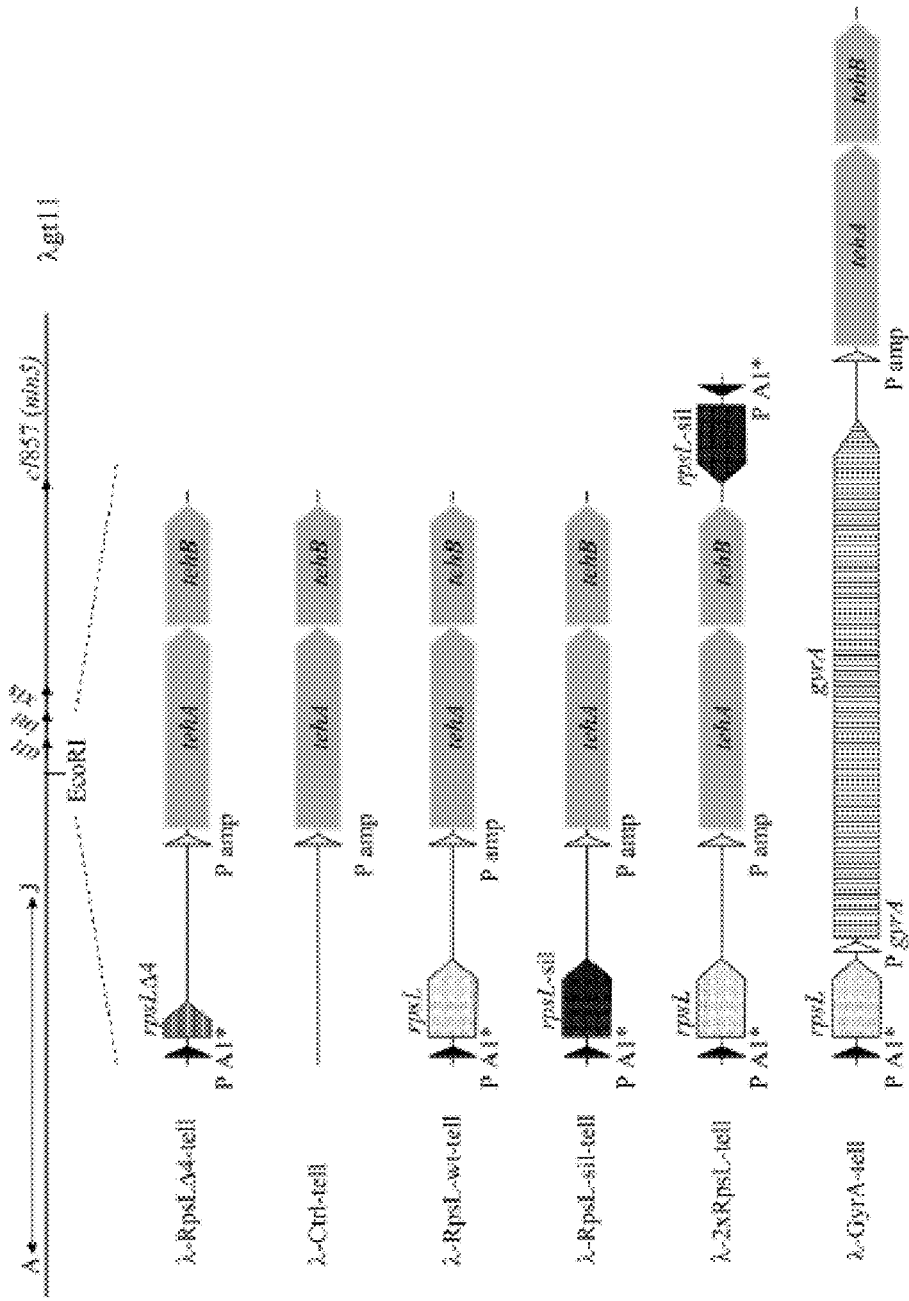

Genetic engineering of the different phages was carried out using λgt11/EcoRI/Gigapack™ III Gold Cloning Kit (Stratagene) according to the manufacturer's protocols. Briefly, EcoRI-digested arms of phage λgt11 were used to construct the lysogenizing phage carrying the different DNA inserts, encoding a chloramphenicol-resistance gene. DNA inserts were PCR amplified from plasmids pRpsL-wt, pRpsL-sil, pRpsLΔ4 (FIG. 1A) using primers 231F/R (Table 4), and digested with MfeI restriction enzyme, which produces ends that are compatible with EcoRI. Ligation was carried out using T4 DNA ligase (New England Biolabs). The ligated products were transformed into E. coli strain Y1088, which supports λgt11 growth. Generated plaques were propagated in E. coli Y1088 or E. coli ymel, which were then used to lysogenize the hosts. In several cases, phages were further manipulated in a host which lacks supE, a suppressor gene necessary for phage growth. In such cases, the phage was transferred by P1-mediated transduction to a permissive host and propagated there. Phages carrying tellurite resistance were constructed by homologous recombination-based genetic engineering of the tellurite-resistance marker instead of the chloramphenicol-resistance gene. The tellurite-resistance genes tehAB were amplified from the E. coli chromosome using primers N1/N2 (Table 4) for λ-RpsLΔ4-tell, λ-RpsL-wt-tell, λ-RpsL-sil-tell, λ-Ctrl-tell, and λ-GyrA-tell (FIG. 1B). Primers RE22/N2 (Table 4) were used for construction of λ-2λxRpsL-tell. The obtained PCR products were used for homologous recombination-based genetic engineering as described below.

Homologous Recombination-Based Genetic Engineering.

Homologous recombination using short-homology flanking ends was performed as known in the art (13). Briefly, an overnight culture of lysogens carrying different DNA inserts encoding the chloramphenicol-resistance gene was diluted 75-fold in 25 ml LB medium with appropriate antibiotics and grown at 32° C. in a shaking water bath to an $OD_{600}$ of 0.6. Then, half of the culture was heat-induced for recombination function of the prophage at 42° C. for exactly 4 minutes in a shaking water bath. The remaining culture was left at 32° C. as the uninduced control. The induced and uninduced samples were immediately cooled on ice slurry and then pelleted at 3600 g at 0° C. for 10 minutes. The pellet was washed twice in ice-cold $ddH_2O$, then resuspended in 200 µl ice-cold $ddH_2O$ and kept on ice until electroporation with ~500 ng of a gel-purified PCR product encoding the tellurite-resistance genes. A 25-µl aliquot of electrocompetent cells was used for each electroporation in a 0.1-cm cuvette at 25 µF, 1.75 kV and 200Ω. After electroporation, the bacteria were recovered in 1 ml LB for 1 hour in a 32° C. shaking water bath and inoculated on selection plates containing 1 to 4 µg/ml tellurite. The DNA insertion into the resulting phages, λ-RpsLΔ4-tell, λ-RpsL-wt-tell, λ-RpsL-sil-tell, λ-Ctrl-tell, λ-GyrA-tell, and λ-2xRpsL-tell, was confirmed by PCR using primer 233F along with 232F or 232R.

Lysogenization.

Overnight culture of the resistant mutants was diluted 1:100 in LB with the appropriate antibiotics, 10 mM $MgSO_4$ and 0.2% (W/V) maltose. When the culture reached an $OD_{600}$ of 0.6-0.8, 100 µl was mixed with 10 µl phage λ, carrying a resistance gene, in a 1.5-ml tube and incubated at room temperature for 20 minutes. Cells were inoculated on appropriate selection plates and incubated overnight at 32° C. Lysogens emerged on selection plates to which the phage carried a resistance gene. Lysogenization was validated by plating the lysogens at 42° C.: lysogens cannot grow at this temperature because the prophage is induced to its lytic cycle.

Transductions.

Transductions were used to transfer antibiotic-resistance markers or complete λ, phages between strains (in cases where the strain did not carry suppressor genes required for λ growth). P1 lysate was prepared as follows: overnight cultures of donor strain were diluted 1:100 in 2.5 ml LB+5 mM $CaCl_2$+0.2 our % (W/V) glucose. After 1 h shaking at 37° C. (or 32° C. for lysogens), $10^7$-$10^8$ PFU of phage P1 was added. Cultures were aerated for 1 to 3 h, until lysis occurred. The obtained P1 lysate was used in transduction where 100 µl fresh overnight culture was mixed with 1.25 µl of 1 M $CaCl_2$ and 0 to 100 µl P1 phage lysate. After incubation for 30 mM at 30° C. without shaking, 100 µl Na-citrate and 500 µl LB were added. Cultures were incubated at 37° C. or 32° C. for 45 or 60 minutes, respectively, then 3 ml of warm LB supplemented with 0.7% agar was added and the suspension was poured onto a plate containing the appropriate drug. Transductants obtained on antibiotic plates were streaked several times on selection plates and verified by PCR for the presence of the transduced DNA fragment.

MIC Determinations.

MIC determination was carried out by following the procedure described by Wiegand et al. (19). Briefly, bacterial cells were grown overnight at 32° C. in LB and diluted to $10^7$-$10^9$ CFU/ml. The obtained suspension was serially diluted 10-fold for different spot concentrations, as indicated. Approximately 1 µl of bacterial suspension was then spotted onto selection plates containing different concentrations of either streptomycin or nalidixic acid along with the appropriate selection agent (chloramphenicol or tellurite), as indicated, using a 48-pin replicator. Plates were incubated overnight and photographed using MiniBis Pro (Bio-Imaging Systems). Photographs were digitally manipulated using GIMP2 software to adjust contrast. Liquid-based MIC determination assays were carried out by inoculating serial dilutions of an antibiotic in liquid LB broth with bacterial cultures ($OD_{600}$ ~0.05) in 96-well microtiter plates. Plates were incubated overnight at 32° C. and $OD_{600}$ was then measured. The lowest antibiotic concentration at which the relative growth compared to the "no-drug" control was below 10% was determined as the MIC.

Example 1

Mutations in the Target Gene, rpsL, Constitute a Major Resistance Mechanism to Streptomycin The overall goal of this study was to provide a proof-of-principle for a genetic system able to restore drug sensitivity to drug-resistant pathogens residing on hospital surfaces. The present inventors chose, as a first step, to use streptomycin as the model drug. Streptomycin is highly useful as an effective antibiotic against both Gram-negative and Gram-positive bacteria. For example, streptomycin is a mainstay of tuberculosis therapy. However, streptomycin-resistant *Mycobacterium tuberculosis* emerge during treatment, and 24 to 85.2% of them have mutations in either rpsL or rrs (15). The rpsL gene product, S12, is an essential, highly conserved protein of the 30S small ribosomal subunit. Most of the acquired resistance to streptomycin is due to specific mutations in rpsL that prevent the inhibitory binding of streptomycin to the essential rpsL gene product. The present inventors wanted to reproduce these findings in a model bacterium, *E. coli*, and then to restore its sensitivity to streptomycin. *E. coli* K-12 were inoculated on LB-agar plates containing 50 µg/ml streptomycin and resistant mutants were selected. This procedure fairly simulates the selection of spontaneous drug-resistant-mutant evolution in hospitals following streptomycin treatment. Resistant colonies emerged with a median frequency of 1 in $10^9$ CFU. Mutations in rpsL were found in 21 out of 22 resistant mutants, a frequency that corroborates with that in clinical isolates. As listed in Table 2, 10 mutants harbored a K88R substitution in RpsL, 6 had an R86S substitution, and P42S, K43L, K43N, R54S, K88E substitutions were each identified once. These mutation types also corroborate with previous studies, confirming that a major mechanism for streptomycin resistance relies on mutations in rpsL (e.g. (16, 18)). Therefore, the present inventors concluded that targeting this resistance mechanism or reversing its effect should prove highly beneficial in controlling drug-resistant pathogens.

Example 2

Wild-Type (wt) rpsL Transformed on a Plasmid Dominantly Confers Streptomycin Sensitivity Minimum inhibitory concentration (MICs) to streptomycin were determined by agar-plate assay (19). In this assay, ~$10^4$ cells are replica-plated on plates with different drug concentrations. The lowest concentration at which there is no visible colony-formation is defined as the MIC. The MICs throughout the study were also measured in a complementary liquid-determination assay, giving a similar readout (not shown). Two representatives of the most common streptomycin-resistant strains obtained above were taken for further study: strains Sm6 and Sm13, harboring mutations in rpsL leading to substitutions of R86S and K88R, respectively. Their MICs to streptomycin were 100 µg/ml and 200 µg/ml, respectively, whereas the MIC of the parental strain was 1.56 µg/ml. These strains were transformed with the plasmid pRpsL-wt, encoding the wt rpsL, or a control plasmid, pRpsLΔ4, encoding a mock gene (a defective rpsL with a 4-bp deletion that disrupts the reading frame after amino acid 26 of the RpsL protein; see FIG. 1) under a modified early *E. coli* promoter from phage T7. Transformed cells were selected on agar plates supplemented with 35 µg/ml chloramphenicol, as the plasmid encodes chloramphenicol acetyl transferase, which confers chloramphenicol resistance. The MICs of the transformed strains to streptomycin were then determined. As shown in FIG. 2A, transformation of the plasmid encoding wt rpsL, pRpsL-wt, conferred a dominant sensitive phenotype, restoring the MIC of the resistant mutants Sm6 and Sm13 from 100 µg/ml to 12.5 µg/ml and from 200 µg/ml to 3.125 µg/ml, respectively. A control, streptomycin-sensitive *E. coli* transformed with these plasmids (pRpsLΔ4 or pRpsL-wt) retained similar MICs to streptomycin (not shown). These results demonstrate that a wt rpsL allele delivered via a plasmid into a streptomycin-resistant *E. coli* renders the cell significantly more sensitive to streptomycin.

Example 3 rpsL Designed with Decreased Homology to the wt Allele can Efficiently Restore Streptomycin Sensitivity The present inventors propose that the rpsL-containing construct may be transferred horizontally between strains by transformation, conjugation or transduction, as described below. Recombination events between the chromosomal resistant rpsL and the delivered wt rpsL may reduce the efficiency of the construct because it may eventually recombine with an rpsL copy that does not confer sensitivity on the transformed strains (nevertheless, there is no danger that it will confer resistance in sensitive strains as the sensitive allele is dominant). In order to reduce the undesired recombination events between the incoming allele conferring sensitivity and the resistant allele in the transformed cell, the present inventors have designed an allele which cannot undergo homologous recombination with the bacterial copy. Efficient homologous recombination requires identity between recombining genes. Reduction of homology from 100% to 90% decreases the frequency of recombination over 40-fold in *E. coli* (14). In addition, a minimal efficient processing segment of 23 to 27 bp that is identical to the invading strand is required for efficient homologous recombination (14). The present inventors synthesized an rpsL gene with silent mutations that maximize the incompatibility of recombination with the sequence of wt rpsL. Silent substitutions were made in every possible case, except where codon usage was less than 10%. Overall, the genes were identical in only 62% of their sequence, and there was no single minimal efficient process segment between the wt rpsL and the new rpsL allele, thus providing efficient barriers against homologous recombination. This allele was designated rpsL-sil, and the plasmid encoding it, pRpsL-sil. The introduced silent mutations might hamper the folding of the encoded protein or its expression levels (3). Therefore, this allele was tested, like the wt rpsL, for its ability to dominantly restore sensitivity. As shown in FIG. 2B, dramatic sensitization to streptomycin was observed, with the MIC values decreasing in Sm6 and Sm13 from 100 µg/ml to 25 µg/ml and from 200 µg/ml to 6.25

µg/ml, respectively. The efficiency of restoration of sensitivity was lower than that observed with the wt rpsL, possibly due to the product's folding efficiency, as already mentioned. Nevertheless, these results indicate that both rpsL and rpsL-sil can efficiently restore sensitivity to streptomycin when expressed from plasmids.

Example 4

A Toxic Compound, Tellurite, Efficiently Replaces Chloramphenicol as a Selection Marker In the above experiments, chloramphenicol, under the constitutive bla promoter, was used as a selection and maintenance marker for the rpsL-encoding plasmids. However, chloramphenicol is not a dispensable antibiotic, and by using it in the proposed system, sensitivity to streptomycin is restored by forfeiting sensitivity to chloramphenicol. This outcome is less desirable than one in which drug sensitivity is restored without forfeiting sensitivities to other drugs. The present inventors therefore sought to replace chloramphenicol with a dispensable, yet efficient, selection substance. A resistance gene against tellurite ($TeO_3^{2-}$), a toxic compound, was evaluated. Tellurite is toxic to bacteria as it forms long-lived sulfur complexes, thus disrupting the thiol balance in the bacterial cells. The tellurite-resistance genes, tehAB, present naturally in the E. coli chromosome, do not confer resistance to E. coli under their endogenous promoter due to low transcription (9). Upon expression from an active promoter (e.g. T7), however, the MIC of tellurite against E. coli increases 50- to 100-fold.

Plasmids encoding rpsL-sil or the mock gene were constructed, carrying the tellurite-resistance genes, tehAB, instead of the gene encoding chloramphenicol acetyl transferase. These plasmids were named pRpsL-sil-tell and pRpsLΔ4-tell. The plasmids were transformed into the streptomycin-resistant strains, Sm6 and Sm13, and the MICs of these transformed cells to streptomycin were determined. Restoration of sensitivity by tellurite-based plasmids was comparable to that observed with the chloramphenicol-based plasmids (FIG. 3). pRpsL-sil-tell sensitized Sm6 from a MIC of 100 µg/ml to 1.56 µg/ml, and Sm13 from a MIC of 200 µg/ml to 12.5 µg/ml. These results indicate that tellurite can be used instead of the chloramphenicol-resistance marker. They also demonstrate that tellurite can maintain the plasmids without cross-reactivity with the streptomycin-resistance phenotype.

Example 5

Streptomycin-Resistant Bacteria Lysogenized with Phage λ Encoding rpsL Become Streptomycin-Sensitive The above experiments show that it is possible to restore drug sensitivity using plasmids as a genetic delivery tool without forfeiting other drugs' efficiencies. The present inventors next evaluated the use of phages as safer delivery vehicles for the designed constructs. We chose λ, a model phage which has been extensively studied, as a gene-delivery tool. This phage can infect its E. coli host and proceed to the lytic to or lysogenic cycle. A common phage mutant was used (λgt11, see Materials and Methods) which is directed to a specific cycle type according to the ambient temperature, and has a deletion (nin5) designed to allow stable insertion of up to 5 kb of foreign DNA. This phage mutant was engineered to contain wt rpsL, rpsL-sil, or a mock-rpsL, each linked to the tellurite-resistance genes and designated, respectively, λ-RpsL-wt-tell, λ-RpsL-sil-tell, and λ-RpsLΔ4-tell. One of the streptomycin-resistant strains used above, Sm13, was lysogenized with the recombinant phages and selected on agar plates supplemented with 1.5 µg/ml tellurite at 32° C., a temperature at which it favors the lysogenic cycle. The lysogenized bacteria were propagated and their MICs to streptomycin determined. Lysogenization of Sm13 by the phages resulted in sensitization of the resistant mutants (FIG. 4A). The MIC value for the λ-RpsLΔ4-tell lysogen was 200 µg/ml, compared to 25 µg/ml and 50 µg/ml for λ-RpsL-wt-tell and λ-RpsL-sil-tell, respectively. Although significant, the sensitization was not as efficient as that observed using plasmid delivery.

Example 6

Two Copies of the rpsL Gene are Significantly More Efficient than a Single Copy in Reversing Resistance It was suspected that the decreased sensitization observed by lysogenization relative to plasmid transformation was due to a lower number of rpsL gene copies introduced by the λ phage. To test this and improve the sensitization, the two different rpsL alleles (wt rpsL and rpsL-sil) were cloned into the λ phage, designated λ-2xRpsL-tell, which was used to lysogenize the resistant strain Sm13 as above. Introduction of two gene copies dramatically enhanced the sensitization efficiency of the lysogenized strains, resulting in a significant decrease of the MIC from 200 µg/ml to 1.56 µg/ml, comparable to the MIC observed for the sensitive strain (FIG. 4B). As a whole, these results constitute a proof-of-principle for restoration of sensitivity to streptomycin using a phage that carries sufficient copies of rpsL, at the "genetic cost" of a resistance marker to a toxic compound.

Example 7

Nalidixic Acid-Resistant Bacteria Lysogenized with Phage λ Encoding gyrA Show Restored Nalidixic Acid Sensitivity The above results demonstrate that streptomycin resistance can be reversed by the proposed system. The present inventors wished to expand the proof-of-principle to other antibiotics as well, to demonstrate that a "multidrug-sensitivity cassette" can theoretically be used. Quinolone resistance was targeted, which also manifests dominant sensitivity by the wt allele (12). The quinolone drug family targets the enzyme gyrase, encoded by gyrA, resulting in DNA-replication arrest. Mutations in gyrA are observed in a specific region termed "quinolone-resistance-determining region" (QRDR). The wt gyrA allele is dominant sensitive and may therefore reverse resistance (12). Nalidixic acid, the first of the synthetic quinolone family antibiotics, was used here as a representative of the quinolone family. To test whether the system can restore sensitivity to quinolone, spontaneous nalidixic acid-resistant mutants were isolated by plating sensitive E. coli on 50 µg/ml nalidixic acid. Similar to the isolation of the streptomycin mutants, mutants were obtained with previously reported substitutions in the target gene, gyrA (Table 3). Five D87G substitutions and three S83L substitutions in the gyrA gene product were identified. These results corroborate another study on pathogenic E. coli, which showed that 37 out of 38 isolated quinolone-resistant gyrA mutants have substitutions at either S83 or D87 or both. Out of 36 pathogenic E. coli resistant to high levels of nalidixic acid (MIC≥256

μg/ml), 35 had at least one mutation in gyrA (4). Here, as with the isolation of streptomycin-resistant mutants, the fact that most of the spontaneous mutants are located in the target gene highlights the potential benefit of reversing the effect of these mutations. The present inventors next introduced the wt gyrA expressed from its endogenous promoter, or a control construct, both linked to tellurite-resistance genes, into λ phages, designated λ-GyrA-tell and λ-Ctrl-tell respectively. These phages were used to lysogenize a nalidixic acid-resistant strain, Nal2, harboring a S83L substitution in GyrA. The lysogens were selected on 4 μg/ml tellurite and tested for sensitization by measuring MICs as described above, using nalidixic acid instead of streptomycin. As shown in FIG. 5, the gyrA construct significantly reversed the mutant's resistance. The MIC of the resistant mutants decreased twofold when lysogenized by a gyrA-encoding phage compared to the control phage. The significance of this sensitization was corroborated by experiments in which gyrA-encoding plasmids were transformed into nalidixic acid-resistant mutants. A three orders of magnitude decrease in the number of CFU on 50 μg/ml nalidixic acid was observed compared to resistant cells transformed with a mock plasmid (FIG. 6). Overall, these results indicate that the proposed system can be used to target nalidixic acid resistance as well as streptomycin resistance.

Example 8

Proposed Application, Safety Measures, and Advantages of the System

The proof-of-principle presented here is a step toward solving the major threat of emerging drug-resistant pathogens, against which there are limited new emerging antibiotic weapons. It demonstrates that with simple genetic engineering, bacteria can be resensitized to approved and useful antibiotics. According to one embodiment, the system can be applied in a simple treatment of hospital surfaces to reverse the resistance of nosocomial pathogens.

The proposed uses and advantages of the system are presented in Table 5, herein below.

TABLE 5

| Advantage of proposed procedure | Proposed procedure | Current procedure | Surface treatment/frequency | |
|---|---|---|---|---|
| Renders bacteria drug-sensitive | V | V | Soap | Floor/furniture cleansing |
| | V | X | Lysogenizing phages | |
| Selects for drug-sensitive residual bacteria to occupy ecological niche | V | V | Disinfectant | Disinfection |
| | V | X | Tellurite | |
| Repeated usage results in more sensitive clones | V | V | Daily | Frequency |

Extended transfer of the sensitizing cassette by specifically constructed lysogenizing phages might enrich for antibiotic-treatable pathogens on hospital surfaces. This enriched, sensitive population might then interfere with the establishment of newly introduced resistant pathogens by overtaking their ecological niche. The present approach differs from conventional phage therapy in the sense that it does not use phages to kill the pathogens directly. Consequently, there is no selection against the used phage, but rather selection for pathogens harboring the phage because it contains tellurite resistance. Moreover, the approach avoids the use of phages inside the patient's body, thus overcoming toxicity issues and other drawbacks of phage therapy, such as phage neutralization by the spleen and the immune system (11).

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A genetically modified bacteriophage comprising:
   (i) an exogenous polynucleotide which encodes at least one agent which reduces the toxicity of a bacterium, is non-toxic to the bacterium and does not affect directly the survival of said bacterium, said polynucleotide is a dominant sensitive antibiotic resistant gene that reverses resistance of said bacterium to an antibiotic, wherein said at least one agent is 30S ribosomal subunit protein S12, encoded by the polynucleotide sequence of SEQ ID NO: 24; and
   (ii) an exogenous polynucleotide which encodes a selectable marker that renders a bacterium infected by said phage resistant to a toxic compound selected from the group consisting of potassium-tellurite, chlorhexidine salts, diamidines, acridines, arsenite, arsenate and antimonite.

2. The bacteriophage of claim 1, wherein said polynucleotide further comprises at least one dominant sensitive antibiotic resistant gene selected from the rpsl gene encoding the 30S ribosomal subunit protein S12, the gyrA gene encoding the gyrase protein, the rpoB gene that encodes the RNA Polymerase β Subunit and the thyA gene that encodes thymidylate synthase.

3. The bacteriophage of claim 2, wherein said resistance is due to a mutated polypeptide of said bacterium selected to be 30S ribosomal subunit protein S12.

4. The bacteriophage of claim 2, wherein said resistance is due to a mutated polypeptide of said bacterium selected to be the gyrase protein.

5. The bacteriophage of claim 2, wherein said at least one dominant sensitive antibiotic resistant gene is a gene encoding a polypeptide selected to be 30S ribosomal subunit protein S12 or the gyrase protein.

6. The bacteriophage of claim 2, wherein said at least one dominant sensitive antibiotic resistant gene is a gene encoding a 30S ribosomal subunit protein S12.

7. The bacteriophage of claim 1, wherein said agent is a polynucleotide agent which down-regulates expression of an antibiotic resistance gene in said bacterium.

8. The bacteriophage of claim 1, wherein said selectable marker comprises a resistance marker to tellurite.

9. The bacteriophage of claim 1, being a lambda temperate phage.

10. An anti-bacterial composition, comprising a carrier and as an active ingredient the bacteriophage of claim 1.

11. The antibacterial composition of claim 10, formulated as a spray, a stick, a paint, a gel, a cream, wash, a wipe, a foam, a soap, an oil, a solution, a lotion, an ointment or a paste.

12. An isolated population of bacterial cells comprising the bacteriophage of claim 1.

13. A kit comprising the phage of claim 1 and a compound which is toxic to bacteria, wherein said toxic compound is selected from the group consisting of potassium-tellurite, chlorhexidine salts, diamidines, acridines, arsenite, arsenate and antimonite.

14. A method of preventing a bacterial infection which is resistant to an antibiotic in a subject, the method comprising contacting a solid surface with an anti-bacterial composition that includes the bacteriophage of claim 1, thereby preventing the bacterial infection.

15. The method of claim 14, further comprising contacting the solid surface with a compound which is toxic to bacteria, said compound is selected from the group consisting of potassium-tellurite, chlorhexidine salts, diamidines, acridines, arsenite, arsenate and antimonite.

16. A genetically modified bacteriophage comprising:
   (i) an exogenous polynucleotide which encodes a polypeptide which reverses resistance of a bacterium to an antibiotic, wherein said polypeptide is 30S ribosomal subunit protein S12, encoded by the polynucleotide sequence of SEQ ID NO: 24; and
   (ii) an exogenous polynucleotide which encodes a selectable marker that renders a bacterium infected by said phage resistant to a toxic compound selected from the group consisting of potassium-tellurite, chlorhexidine salts, diamidines, acridines, arsenite, arsenate and antimonite.

17. A genetically modified bacteriophage comprising an exogenous polynucleotide which encodes at least one polypeptide which reverses resistance of a bacterium to an antibiotic and is non-toxic to the bacterium, wherein said wherein said at least one polypeptide is 30S ribosomal subunit protein S12, encoded by the polynucleotide sequence of SEQ ID NO: 24.

18. The bacteriophage of claim 17, wherein said polynucleotide further comprises at least one dominant sensitive antibiotic resistant gene selected from the rpsl gene encoding the 30S ribosomal subunit protein S12, the gyrA gene encoding the gyrase protein, the rpoB gene that encodes the RNA Polymerase β Subunit and the thyA gene that encodes thymidylate synthase.

19. The bacteriophage of claim 17, wherein said polynucleotide further comprises a dominant sensitive antibiotic resistant gene encoding a gyrase protein.

20. The bacteriophage of claim 19, wherein said exogenous polynucleotide further encodes a selectable marker.

21. An anti-bacterial composition, comprising a carrier and as an active ingredient the bacteriophage of claim 19.

22. A method of preventing a bacterial infection which is resistant to an antibiotic in a subject, the method comprising contacting a solid surface with an anti-bacterial composition that includes the bacteriophage of claim 19, thereby preventing the bacterial infection.

23. A genetically modified bacteriophage comprising an exogenous polynucleotide which encodes a polypeptide which reverses resistance of a bacterium to an antibiotic, wherein said polypeptide is the 30S ribosomal subunit protein S12 and is encoded by the polynucleotide sequence of SEQ ID NO: 24.

24. The bacteriophage of claim 23, wherein said exogenous polynucleotide further encodes a selectable marker.

25. The bacteriophage of claim 24, wherein said selectable marker comprises a resistance marker to tellurite.

26. The bacteriophage of claim 23, being a lambda temperate phage.

27. An anti-bacterial composition, comprising a carrier and as an active ingredient the bacteriophage of claim 23.

28. The antibacterial composition of claim 27, formulated as a spray, a stick, a paint, a gel, a cream, wash, a wipe, a foam, a soap, an oil, a solution, a lotion, an ointment or a paste.

29. A method of preventing a bacterial infection which is resistant to an antibiotic in a subject, the method comprising contacting a solid surface with an anti-bacterial composition that includes the bacteriophage of claim 23, thereby preventing the bacterial infection.

30. The method of claim 29, further comprising contacting the solid surface with a compound which is toxic to bacteria said compound is selected from the group consisting of potassium-tellurite, chlorhexidine salts, diamidines, acridines, arsenite, arsenate and antimonite.

31. The method of claim 30, wherein said exogenous polynucleotide further encodes a selectable marker that renders a bacterium infected by said phage insensitive to said toxic compound.

* * * * *